US006329344B1

(12) United States Patent
Arora et al.

(10) Patent No.: US 6,329,344 B1
(45) Date of Patent: Dec. 11, 2001

(54) DERIVATIVES OF MONOSACCHARIDES AS CELL ADHESION INHIBITORS

(75) Inventors: Sudershan K. Arora, Gurgaon; Madan P. Tanwar, Kurukshetra; Jang P. Gupta, Gurgaon; Geeta Sharma, New Delhi, all of (IN)

(73) Assignee: Ranbaxy Laboratories Limited, New Dehli (IN)

( * ) Notice: Subject to any disclaimer, the term of this patent is extended or adjusted under 35 U.S.C. 154(b) by 0 days.

(21) Appl. No.: 09/411,357

(22) Filed: Oct. 1, 1999

Related U.S. Application Data

(63) Continuation-in-part of application No. 09/229,155, filed on Jan. 12, 1999, now abandoned.

(30) Foreign Application Priority Data

Oct. 22, 1998 (IN) .............................................. 3108/DEL/98

(51) Int. Cl.$^7$ .............................. A61K 31/70; C07H 15/00

(52) U.S. Cl. ................................. 514/25; 514/2; 536/4.1; 536/17.2; 536/18.7

(58) Field of Search ..................................... 536/4.1, 17.2, 536/18.7; 514/2, 25

(56) References Cited

U.S. PATENT DOCUMENTS

| 2,715,121 | 8/1955 | Glen et al. | 536/120 |
|---|---|---|---|
| 4,056,322 | 11/1977 | Gordon et al. | 536/4 |
| 4,429,117 | 1/1984 | Koebernick et al. | 536/17.2 |
| 4,735,934 | 4/1988 | Gordon et al. | 514/25 |
| 4,996,195 | 2/1991 | Ronsen et al. | 514/23 |
| 5,010,058 | 4/1991 | Ronsen et al. | 514/23 |
| 5,298,494 | 3/1994 | Arora et al. | 514/23 |
| 5,360,792 | 11/1994 | Arora et al. | 514/23 |
| 5,360,794 | 11/1994 | Arora et al. | 514/25 |
| 5,367,062 | 11/1994 | Arora et al. | 514/25 |
| 5,637,570 | 6/1997 | Arora et al. | 514/25 |
| 5,654,282 | * 8/1997 | Tang et al. | 514/25 |
| 5,795,958 | * 8/1998 | Rao et al. | 530/331 |
| 5,919,769 | * 7/1999 | Tsukida et al. | 514/25 |

FOREIGN PATENT DOCUMENTS

| WO 92/00995 | 1/1992 | (WO) . |
| WO 92/14745 | 9/1992 | (WO) . |
| WO 93/13117 | 7/1993 | (WO) . |
| WO 98/41215 | 9/1998 | (WO) . |

OTHER PUBLICATIONS

Hasegawa et al., J. Carbohydrate Chemistry, Synthesis of N–[2–S–(2–Acetamido–2, 3–Dideoxy–D–Glucopyranose–3–yl)–2–Thio–D–Lactoyl] –L–Alanyl–D–Isoglutamine (1984), 331–341.

N. K. Richimyer Methods in Carbohydrate Chemistry, Monosaccharides, 1962, 107–113.

Aspinall et al., Canadian Journal of Chemistry, The hex–5–enose degradation: zinc dust cleavage of 6–deoxy–6–iodo–D–galactopyranosidic linkages in methylated di–and trisaccharides 1984 ,62, 2728–2735.

S.S. Bhattacharjem and P.A. J. Gorin, Hydrogenolysis of carbohydrate acetals, ketals, and cyclic orthoesters with lithium aluminium hydride—aluminium trichloride, 1969, 1195.

J.F. King and A.D. Allbutt, Remarkable stereoselectivity in the hydrolysis of dioxolenium ions and orthoesters fused to anchored six–membered rings, Canadian Journal of Chemistry, 1970, 48, 1754.

J.F. King and A.D. Allbutt, Stereochemistry of biomolecular nucleophilic opening of a dioxolenium ring fused to an anchored cyclohexane system, Canadian Journal of Chemistry, May 1969, 47, 1455.

Podolsky, Daniel, Attenuation of Colitis in the Cotton–top Tamarin by Anti–4 integrin Monoclonal Antibody, Jul. 1993, 92, 372–380.

Binkley, Roger, Synthesis of methyl 2,6–Dideoxy–3–C–Methyl–α–D–Ribo–Hexopyranoside (Methyl –D–Mycaroside), A component of the antitumor Agent Mithramycin, 1985, 4, 227.

Ferguson, Thomas, Two integrin–binding peptides abrogate T cell–mediated immune responses in vivo, Proc. Natl. Acad. Sci., Sep. 1991, 88, 8072–8076.

Xiao–Dong Yang, Inhibition of insulitis and prevention of diabetes in nonobese diabetic mice by blocking L–selectin and very late antigen 4 adhesion receptors, Proc. Natl. Acad. Sci., Nov. 1993, 90, 10494–10498.

Yednock, Ted, Prevention of experimental autoimmune encphalomyelitis by antiboes against 4 1 integrin, Nature, Mar. 1992, 356, 63–66.

Chisholm, Patricia, Monoclonal antibodes to the integgrin –4 subunit inhibit the murine contact hypersensitivity response, Eur. J. Immunol. 1993, 23, 682–688.

(List continued on next page.)

*Primary Examiner*—Kathleen Kahler Fonda
(74) *Attorney, Agent, or Firm*—Jayadeep R. Deshmuhk, Esq.

(57) ABSTRACT

The present application relates to a group of novel substituted pentose and hexose monosaccharide derivatives, not previously disclosed, which exhibit potent anti-cell adhesion and anti-inflammatory activities. Methods of preparation, pharmaceutical compositions containing the compounds and methods of treatment, suppression and prevention of cell adhesion mediated chronic inflammatory disorders are also described.

22 Claims, No Drawings

OTHER PUBLICATIONS

Nowlin, Dawn, A Novel Cyclic Pentapeptide Inhibits 3 1 and 5 1 Integrin–mediated Cell Adhesion, The Journal of Biological Chemistry, Sep. 1993, 266, 27, 20352–20359.

Baron, Jody, Surface Expression of 4 Integrin by CD4 T Cells Is Required for Their Entry into Brain Parenchyma, J. Exp. Med.., Jan. 1993, 177, 57–58.

Komoriya, Akira, The Minimal Essential Sequence for a Major Cell Type–specific Adhesion Site (CS1) within the Alternatively Spliiced Type III Connecting Segment Domain of Fibronectin Is Leucine–Aspartic Acid–Valine, Journal of Biological Chemistry, Aug. 1991, 266, 23, 15075–15079.

Wahl, S.M., Synthetic Fibronectin Peptides Suppress Arthritis in Rats by Interrupting Leukocyte Adhesion and Recruitment, The Journal of Clinical Investigation, Aug. 1994, 94, 655–662.

Abraham, William, –Integrins Mediate Antigen–induced Late Bronchial Responses and Prolonged Airway Hyperresponsiveness in Sheep, The Journal of Clinical Investigation, Feb. 1994, 93, 776–787.

O.T. Schmidt, Methods in Carbohydrate Chemistry, Monosaccharides, 1962, 191–194.

* cited by examiner

DERIVATIVES OF MONOSACCHARIDES AS CELL ADHESION INHIBITORS

CROSS-REFERENCE TO RELATED APPLICATION

This application is a continuation-in-part of Ser. No. 09/229,155 filed Jan. 12, 1999 now abandoned.

FIELD OF INVENTION

This invention generally relates to the derivatives of 5,6-dideoxy-α,D-5-epiglucofuranose, 5,6-dideoxy-α,D-5-epiallofuranose, 5,6-dideoxy-α,D-5-epimannofuranoside, 5-deoxy-α,D-lyxofuranoside, 5-deoxy-α,D-xylofuranose, 5-deoxy-α,D-ribofuranose, or 2,3-isopropylidene-α-L-xylo-2-hexulofuranosonic acid and processes for the preparation thereof.

The compounds of this invention are useful, inter-alia, for the inhibition and prevention of cell adhesion and cell adhesion-mediated pathologies, including inflammatory and autoimmune diseases, such as bronchial asthma, rheumatoid arthritis, type I diabetes, multiple sclerosis, allograft rejection, and psoriasis.

This invention also relates to pharmacological compositions containing the compounds of the present invention and the methods of treating such pathologies as listed above.

BACKGROUND OF THE INVENTION

Cell adhesion is a process by which cells associate with each other, migrate towards a specific target localized within the extracellular matrix. Specialized molecules, called cell adhesion molecules (CAMs), mediate these interactions. CAMs have been demonstrated to participate in various cell-cell, cell-extracellular matrix, and platelet-platelet interactions. CAMs influence the leukocytes' adhesion to the vascular endothelium, their transendothelial migration, retention at extravascular sites, and activation of T cells and eosinophils. These processes are central to the pathogenesis of inflammatory and autoimmune diseases. Therefore, CAMs are considered potential targets in treating such disorders.

CAMs can be classified into three groups: integrins, selectins, and the immunoglobulin superfamily. Of these, integrins are key mediators in the adhesive interactions between hemopoietic cells and their microenvironment. They are comprised of alpha-beta heterodimers that integrate signals from the outside to the inside of cells, and vice versa. Integrins can be classified on the basis of the beta subunits they contain. For example, beta-1 integrins comprise the beta-1 subunit noncovalently linked to one of the 10 different alpha subunits.

The alpha-4 beta-1 integrin, also known as $VLA_4$ (very late activation antigen 4), is a member of the beta-1 integrin family and comprises alpha-4 and beta-1 subunits. $VLA_4$ interacts with two specific ligands—the vascular cell adhesion molecule (VCAM-1) and the CS1 region of the protein fibronectin. Adhesion mediated by $VLA_4$ is central to the process of transendothelial migration of leukocytes. Ligation of $VLA_4$ is followed by gross rearrangement of the cytoskeleton, leading to flattening of cells along the blood vessel wall, followed by expression of specific molecules that digest the endothelial cell wall and diapedesis. Once in the extraluminal region, the interactions of $VLA_4$ with extracellular fibronectin play a crucial role in the migration of leukocytes to the site of inflammation, T cell proliferation, and expression of cytokines and inflammatory mediators.

Additionally, $VLA_4$ ligation provides co-stimulatory signals to the leukocytes, resulting in enhanced immunoreactivity. Thus, appropriate $VLA_4$ antagonists would, in theory, ameliorate the immune response through a twofold action-inhibition of T cell recruitment at the site of inflammation and inhibition of co-stimulatory activation of immune cells.

In this respect, inhibitors of $VLA_4$ interactions have been demonstrated to show beneficial therapeutic effects in several animal models of inflammatory and allergic diseases, including sheep allergic asthma (Abraham et al, J. Clin. Invest. 1994;93:776); arthritis (Wahl et al, J. Clin. Invest. 1994;94:655); experimental allergic encephalomyelitis (Yednock et al, Nature (Lond) 1992;356:63 and Baron et al, J. Exp. Med. 1993;177:57); contact hypersensitivity (Chisolm et al, Eur J. Immunol. 1993;23:682); type I diabetes (Yang et al, Proc. Natl. Acad. Sci. (USA) 1993;90:10494), and inflammatory bowel disease (Podolsky et al, J. Clin. Invest. 1993;92:372).

The CS1 moiety region of fibronectin involved in the interaction with $VLA_4$ was identified as the tripeptide Leucyl-Aspartyl-Valyl (LDV) (Komoriya et al, J. Biol. Chem. 1991;266:15075). Several peptides containing the LDV sequence were synthesized and also shown to inhibit the in vivo interaction of $VLA_4$ to its ligands (Ferguson et al, Proc. Natl. Acad. Sci., USA, 1991;88:8072; Wahl et al, J. Clin. Invest. 1994;94:655; Nowlin et al, J. Biol. Chem. 1993;268(27):20352; and PCT application PCT/US91/04862).

Despite these advances, a need for small and specific inhibitors of $VLA_4$-dependent cell adhesion molecules remains. Ideally, such inhibitors are water soluble with oral efficacy. Such compounds would provide useful agents for treatment, prevention, or suppression of various inflammatory pathologies mediated by $VLA_4$ binding.

It is generally known that isopropylidene and benzylidene groups are the most commonly used protective groups in carbohydrate chemistry. Although both these groups are introduced into a molecule under similar conditions, the location of the protection can be quite different. The reason for this difference is directly related to the stability of each protected molecule. Since protection normally occurs under conditions that allow reversibility, the reaction proceeds until equilibrium is reached. The distribution of products at equilibrium is determined by their relative thermodynamic stabilities. In other words, these reactions are thermodynamically controlled. Benzylidene groups prefer to be part of 6-membered ring acetals, while the ketals resulting from acetonation generally are 5-membered rings. The difference is attributed to the effect of the methyl and phenyl substituents on the stability of the particular ring systems. These blocking methods are described in U.S. Pat. Nos. 2,715,121, 4,056,322, 4,735,934, 4,996,195, and 5,010,058, the disclosures of which are incorporated herein by reference. Other blocking methods are also described in J. Carbohydr. Chem., 1985;4:227 and 1984;3:331; Methods in Carbohydr. Chem. 1962;1:191 and 1962;1:107; Can J. Chem. 1984;62:2728, 1969;47:1195, 1455, and 1970;48:1754, all incorporated herein by reference. The prior art reveals that D-glucose is blocked at the 1,2;5,6-positions with isopropylidene or cyclohexylidene blocking group with the 3-position left open to undergo derivatization. The therapeutic activity of hexoses and their derivatives is also disclosed in some of the above-cited prior art.

The compounds of the present invention were screened for inhibitory activity in $VLA_4$-mediated cell adhesion assay and the classical murine hypersensitivity assay in mice.

Several compounds exhibited significant inhibitory activity in both tests. The salts of these compounds could be easily solubilized in water and used in the treatment of chronic, cell adhesion-mediated, allergic, autoimmune and inflammatory disorders, such as bronchial asthma and rheumatoid arthritis. Some of the prior art describes development of peptide derivatives as cell adhesion antagonists for treatment of these diseases. However, because treatment of chronic diseases requires prolonged (mid-term to long-term) administration of drugs, the development of small molecules, i.e., specific orally-available inhibitors of cell adhesion, would be very beneficial.

There is no example available in the prior art wherein the compounds of the present invention, containing a sugar nucleus coupled with a urea moiety, are used as therapy for the inhibition, prevention, and suppression of $VLA_4$-mediated cell adhesion and pathologies associated with that adhesion.

SUMMARY OF THE INVENTION

An object of the present invention is to provide a new class of compounds that exhibit significant activity as $VLA_4$ antagonists.

Intermediates mentioned in U.S. Pat. Nos. 4,996,195, 5,637,570, 5,367,062, 5,360,794, 5,360,792, 5,298,494 and 5,010,058 were used as core nuclei and prepared similarly as described in these patents. However, in the present application it has been discovered that the introduction of urea moiety at various positions of pentose and hexose monosaccharides introduces $VLA_4$ antagonism activity. It was also discovered that the sequence Leucyl-Aspartyl-Valyl-Prolyl (LDVP) or any other amino acid, dipeptide, or tripeptide as present in fibronectin are not necessary for the compounds to be active as inhibitors of $VLA_4$.

It is a further object of this invention to provide novel carbohydrate-based water-soluble compounds, which exhibit significant activity to be used as cell adhesion antagonists.

Other objects and advantages of the invention will be set forth in the description that follows, will be in part apparent from the description, or may be learned by the practice of the invention. The objects and advantages of the invention may be realized and obtained by means of the mechanisms and combinations pointed out in the appended claims.

In order to achieve the above-mentioned objects and in accordance with one aspect of the present invention, there is provided a compound having the structure of Formula I:

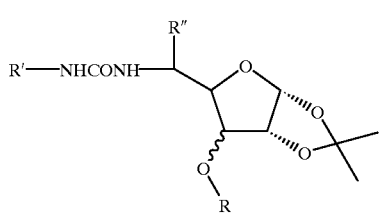

Formula I and its pharmaceutically acceptable salts, esters, enantiomers, diastereomers, N-oxides, amides, prodrugs, or metabolites, wherein R is $C_1$ to $C_{15}$ alkyl, alkene, alkyne (straight chain or branched), aryl, substituted aryl or alkylaryl, R' is $SO_2C_6H_5$, $SO_2C_6H_4CH_3$-p, or $SO_2C_6H_4Cl$-p, phenyl or substituted phenyl, represented as $C_6H_4$-R'''-p, R''' being Cl, $NO_2$, $OCH_3$, $CH_3$, $CH_2COOH$, $CH_2COOCH_3$, $CH_2COLDVP$, $CH_2CODVP$, $CH_2COVP$, wherein LDVP, DVP and VP represent tetrapepide (Leucyl-aspartyl-valyl-prolyl), tripeptide (aspartyl-valyl-prolyl) and dipeptide (valyl-prolyl), respectively, R'' is H or $CH_3$, and (~~~) represents epiglucofuranose, epiallofuranose, xylofuranose or ribofuranose configurations, and methods of manufacturing such compounds.

In accordance with a second aspect of the present invention, there is provided a compound having the structure of Formula II comprising epimannofuranoside or lyxofuranoside derivatives,

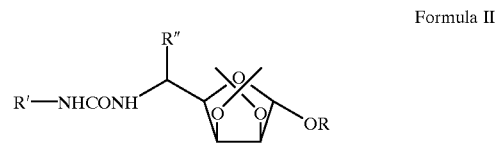

Formula II and its pharmaceutically acceptable salts, esters, enantiomers, diastereomers, N-oxides, amides, prodrugs, or metabolites, wherein R is $C_1$ to $C_{15}$ alkyl, alkene, alkyne (straight chain or branched), aryl, substituted aryl or alkylaryl, R' is $SO_2C_6H_5$, $SO_2C_6H_4CH_3$-p, or $SO_2C_6H_4Cl$-p, phenyl or substituted phenyl, represented as $C_6H_4$-R'''-p, R''' being Cl, $NO_2$, $OCH_3$, $CH_3$, $CH_2COOH$, $CH_2COOCH_3$, $CH_2COLDVP$, $CH_2CODVP$, $CH_2COVP$, wherein LDVP, DVP and VP represent tetrapepide (Leucyl-aspartyl-valyl-prolyl), tripeptide (aspartyl-valyl-prolyl) and dipeptide (valyl-prolyl), respectively, R'' is H or $CH_3$, and methods of manufacturing such compounds.

In accordance with a third aspect of the present invention, there is provided a compound having the structure of Formula III:

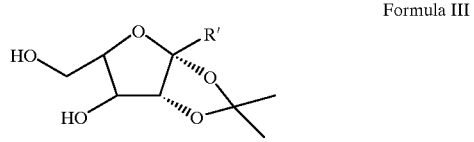

Formula III and its pharmaceutically acceptable salts, esters, enantiomers, diastereomers, N-oxides, amides, prodrugs, or metabolites, wherein R' is COLDVP, CODVP, COVP or $CH_2$-NH-CO-NHR'', wherein LDVP, DVP and VP represent tetrapepide (Leucyl-aspartyl-valyl-prolyl), tripeptide (aspartyl-valyl-prolyl) and dipeptide (valyl-prolyl), respectively, and wherein R'' is $C_6H_4R'''$-p (R''' is Cl, $NO_2$, $OCH_3$, $CH_3$, $CH_2COOH$, $CH_2COLDVP$, $CH_2CODVP$ or $CH_2COVP$), and methods of manufacturing such compounds.

In accordance with a fourth aspect of the present invention, there is provided a list of compounds as shown below in the description of the invention section.

In accordance with a fifth aspect of the present invention, there are provided methods of preventing, inhibiting, or suppressing cell adhesion in an animal, the term animal as defined herein includes human or mammal, comprising administering to said animal compounds as described above.

In accordance with a sixth aspect of the present invention, there are provided methods for treating animals suffering from bronchial asthma, rheumatoid arthritis, multiple sclerosis, type I diabetes, psoriasis, allograft rejection, and other inflammatory and/or autoimmune disorders, comprising administering to said animals compounds as described above.

In accordance with a seventh aspect of the present invention, there is provided a method for preventing, inhibiting, or suppressing cell adhesion-associated inflammation, immune or autoimmune response with compounds as described above.

In accordance with an eighth aspect of the present invention, there is provided a method for treating or preventing a disease selected from the group consisting of asthma, arthritis, psoriasis, transplantation rejection, multiple sclerosis, diabetes and inflammatory bowel disease with compounds as described above.

DETAILED DESCRIPTION OF THE INVENTION

The compounds of the present invention may be prepared by techniques well known in the art and familiar to the average synthetic organic chemist. In addition, the compounds of the present invention may be prepared by the following novel and inventive reaction sequences, which also show preferred R, R', R", R''' and (∿∿) groups.

SCHEME 1

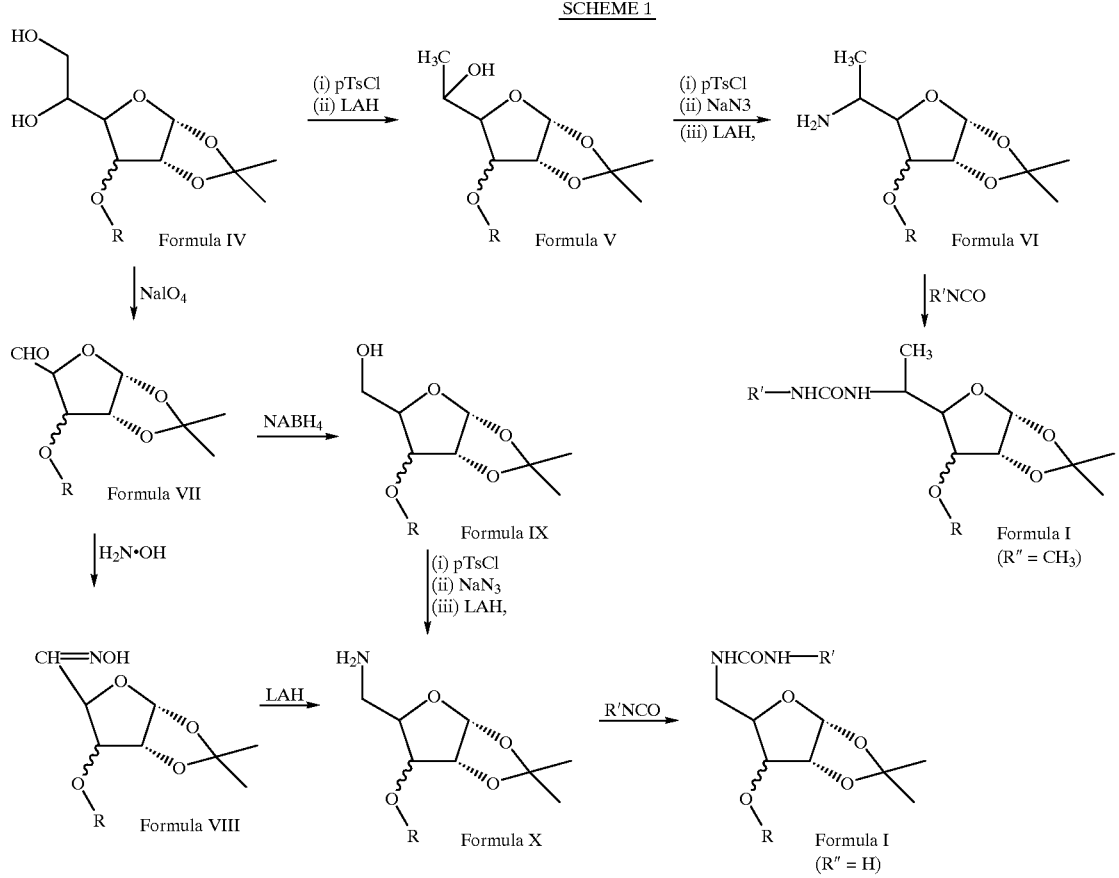

In accordance with a ninth aspect of the present invention, there are provided processes for preparing compounds as described above.

Soluble salts of the above compounds were obtained by the addition of various bases, including TRIS [tris (hydroxymethylaminomethane)] or alkaline hydroxides, carbonates or bicarbonates, etc., and are also included in the invention.

The compounds of the present invention are novel and exhibit significant potency in terms of their activity, which was determined by in vitro $VLA_4$-mediated cell adhesion assay and in vivo mouse ear swelling test. The compounds that were found active in in vitro assay were tested in vivo. Some of the compounds of the present invention were found to be potent $VLA_4$ antagonists. Therefore, the present invention provides the pharmaceutical compositions for the possible treatment of bronchial asthma, and inflammatory and autoimmune disorders. In addition, the compounds of the above invention can be administered orally or parenterally.

wherein R is $C_1$ to $C_{15}$ alkyl, alkene, alkyne (straight chain or branched), aryl, substituted aryl or alkylaryl and R' is $SO_2C_6H_5$, $SO_2C_6H_4CH_3$-p, $SO_2C_6H_4Cl$-p, phenyl or substituted phenyl of the formula

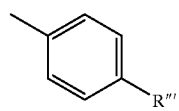

wherein R''' is Cl, $NO_2$, $OCH_3$, $CH_3$, $CH_2COOH$, $CH_2COOCH_3$, $CH_2COLDVP$, $CH_2CODVP$, or $CH_2COVP$ and (∿∿) represents epiglucofuranose, epiallofuranose, xylofuranose or ribofuranose configurations.

In Scheme 1, 1,2-O-isopropylidene-6-deoxy-3-O-alkyl, alkene, alkyne (straight chain or branched), aryl, substituted aryl or alkylaryl glucofuranose or allofuranose were prepared as described in U.S. Pat. No. 5,010,058. This compound, on treatment with p-toluenesulfonyl chloride in pyridine at 0–10° C., gave the corresponding tosyl derivative of Formula V at 5-position which, on treatment with sodium azide (NaN$_3$), undergoes SN$_2$ displacement to afford 5,6-dideoxy epiglucofuranose and 5,6-dideoxy epiallofuranose derivatives. This azide, on reduction with lithium aluminium hydride (LAH), afforded the desired amine of Formula VI, which was subsequently reacted with desired isocyanates to obtain the compounds of Formula I (R″=CH$_3$).

Similarly, 1,2-O-isopropylidene-3-O-alkyl, alkene, alkyne (straight chain or branched), aryl, substituted aryl or alkylaryl α,D-glucofuranose or α,D-allofuranose of Formula IV was oxidized with sodium periodate (NaIO$_4$), followed by reduction with sodium borohydrate (NaBH$_4$) to obtain the corresponding α,D-xylofuranose or α,D-ribofuranose derivatives of Formula IX. This intermediate was tosylated, then subjected to reaction with NaN$_3$, and followed by reduction with LAH to obtain the desired amine. Alternatively, this compound was also prepared by reacting 1,2-O-isopropylidene-4-carboxaldehyde-α,D-glucofuranose or allofuranose of Formula VII with hydroxyl amine (NH$_2$OH) followed by reduction with LAH. This amine compound of Formula X was then treated with suitable isocyanates to obtain the desired compound of Formula I (R″=H).

Similarly, this amine of Formula X was reacted with suitable sulfonylisocyanates to obtain the corresponding sulfonylureido compounds of Formula I (wherein R′ is SO$_2$C$_6$H$_5$, SO$_2$C$_6$H$_4$Cl-p, or SO$_2$C$_6$H$_4$CH$_3$-p). When R′ is —C$_6$H$_4$—CH$_2$—COOCH$_3$, corresponding free carboxylic acid was obtained by hydrolysis with aqueous sodium hydroxide (NaOH), followed by acidification with diluted acid to pH 3.

Compounds of Formula I having the following structure,

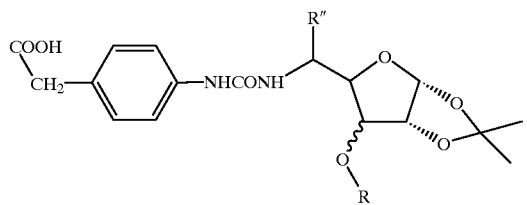

were also coupled with tetrapeptide [Leucyl-aspartyl(OBzl)-valyl-prolyl(OBzl)] or tripeptide [aspartyl-(OBzl)-valyl-prolyl-(OBzl)] or dipeptide [Valyl-prolyl(OBzl)] in the presence of 1-(3-dimethylaminopropyl)-3-ethylcarbodiimide hydrochloride (EDC) or 1,3-dicyclohexylcarbodiimide (DCC) and a suitable base followed by reduction with hydrogen gas (H$_2$) in the presence of Palladium/Carbon (Pd/C) to ascertain the VLA$_4$ properties of these compounds. This LDVP sequence was selected from fibronectin.

SCHEME 2

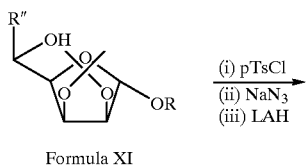

Formula XI

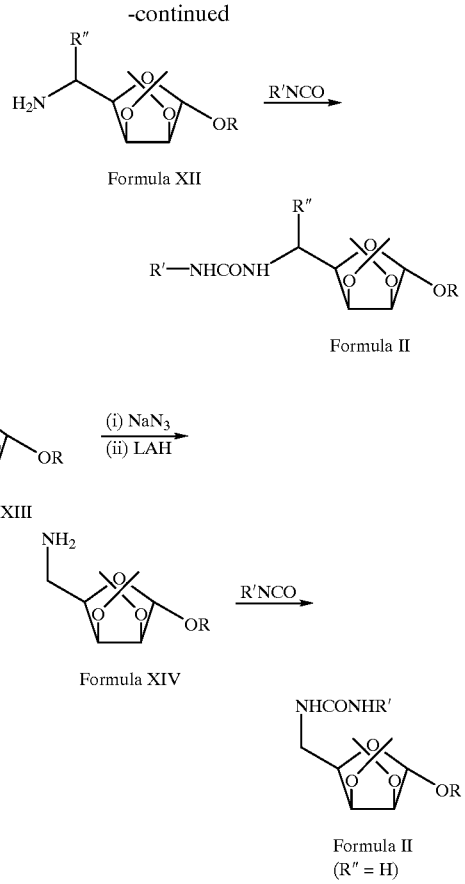

wherein R, R′ and R″ is same as defined in Scheme 1.

Similarly, the compounds synthesized in Scheme 2 are obtained by using α,D-mannose instead of dextrose. Hence 2,3-O-isopropylidene-6-deoxy-1-O-alkyl, alkene, alkyne (straight chain or branched), aryl, substituted aryl or alkylaryl mannofuranoside, of Formula XI as described in the U.S. Pat. No. 5,360,794, was treated with tosyl chloride, followed by the reaction with NaN$_3$ and then reduction with LAH, afforded the corresponding 5-deoxy-5-amino epimannofuranoside derivative of Formula XII, which was treated with suitable alkyl or aryl or substituted aryl isocyanates to afford the compounds of Formula II, wherein R, R′, and R″ have the meanings defined earlier. When R′ is —C$_6$H$_4$—CH$_2$—COOCH$_3$, the corresponding free carboxylic acid was obtained by hydrolysis with aqueous NaOH.

Similarly, 2,3-O-isopropylidene-5-deoxy-1-O-(alkyl, alkene, alkyne (straight chain or branched), aryl, substituted aryl or alkylaryl)-5-tosyl-α,D-lyxofuranoside of Formula XIII (prepared similarly as described in U.S. Pat. No. 5,367,062) was treated with NaN$_3$ followed by reduction with LAH to afford the desired amine of Formula XIV, which was subsequently treated with suitable isocyanates to obtain the desired ureido compounds of Formula II (R″—H).

Similarly, this amine was reacted with suitable sulfonyl-isocyanates to obtain the corresponding sulfonylureido compounds wherein R is SO$_2$C$_6$H$_5$, SO$_2$C$_6$H$_4$Cl-p, or SO$_2$C$_6$H$_4$CH$_3$-p). When R′ is —C$_6$H$_4$—CH$_2$—COOCH$_3$, the corresponding free carboxylic acid was obtained by hydrolysis with aqueous NaOH.

SCHEME 3

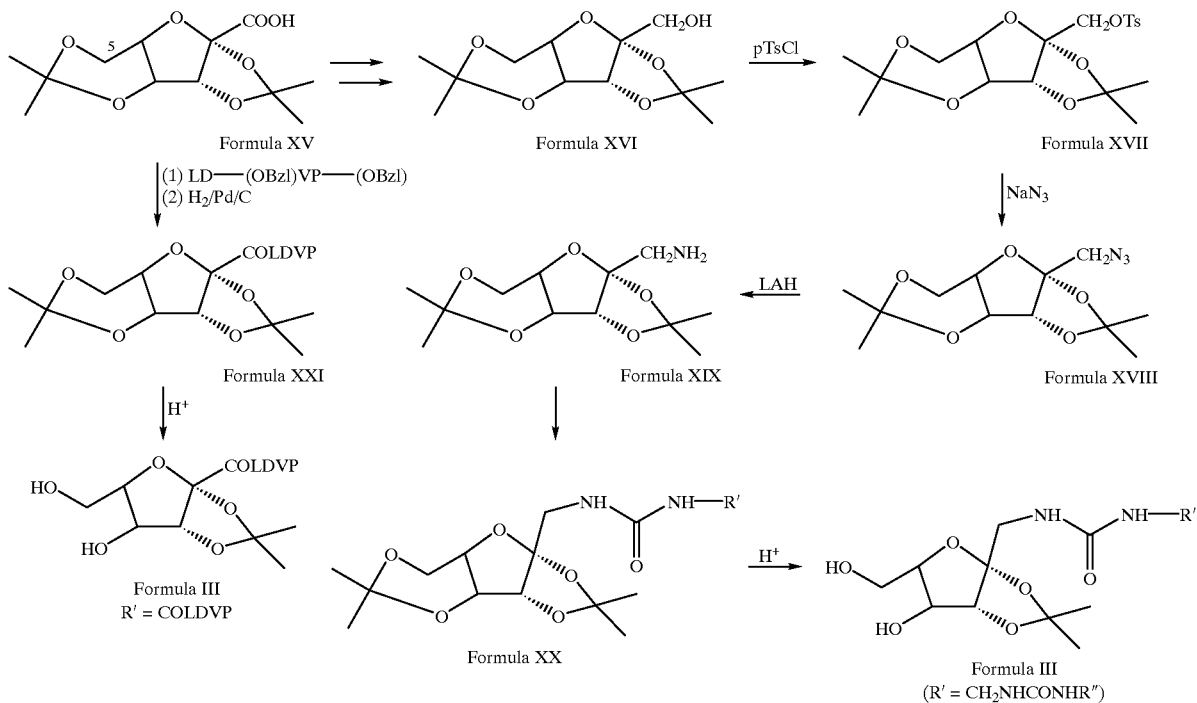

wherein R' is same as defined in Scheme 1.

In Scheme 3, 2,3;4,6-Di-O-isopropylidene-α,L-xylo-2-hexulofuranose of Formula XVI was treated with p-toluenesulfonic acid chloride followed by reaction with sodium azide and LAH to obtain the corresponding 1-amino derivative of Formula XIX. This compound was treated with the suitable isocyanate to give compounds of Formula XX followed by selective hydrolysis of 4,6 positions to obtain the desired compounds of Formula III.

2,3;4,6-Di-O-isopropylidene-α,L-xylo-2-hexulofuranosonic acid of Formula XX was reacted with LD(OBzl)VP(OBzl) followed by hydrogenation and selective hydrolysis with perchloric acid to obtain the compounds of Formula III (R'=COLDVP).

The compound of Formula XX having the following structure

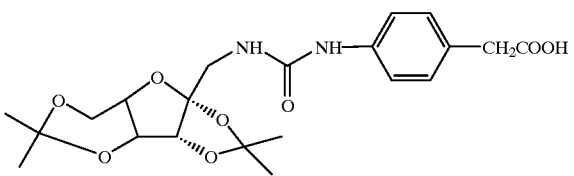

was also coupled with tetrapeptide [Leucyl-aspartyl(OBzl)-valyl-prolyl(OBzl)] or tripeptide [aspartyl(OBzl)-valyl-prolyl(OBzl)] or dipeptide [Valyl-prolyl(OBzl)] in the presence of EDC or DCC and a suitable base followed by reduction with $H_2$ in the presence of Pd/C to ascertain the $VLA_4$ properties of these compounds.

Suitable salts such as TRIS, sodium, potassium, ammonium, etc. were prepared so as to solubilize the compound in aqueous medium for biological evaluations.

Preferred compounds according to the invention and capable of being produced by Schemes 1 through 3 include:

1,2-O-isopropylidene-3-O-dodecyl-5,6-dideoxy-5-N-{[4-(2-hydroxy-2-oxoethyl)phenyl]aminocarbonyl amino}-α,D-5-epiglucofuranose (compound 1)

1,2-O-isopropylidene-3-O-decyl-5,6-dideoxy-5-N-{[4-(2-hydroxy-2-oxoethyl)phenyl]aminocarbonylamino}-α,D-5-epiglucofuranose (compound 2)

1,2-O-isopropylidene-3-O-heptyl-5,6-dideoxy-5-N-{[4-(2-hydroxy-2-oxoethyl)phenyl]aminocarbonylamino}-α,D-5-epiglucofuranose (compound 3)

1,2-O-isopropylidene-3-O-butyl-5,6-dideoxy-5-N-{[4-(2-hydroxy-2-oxoethyl)phenyl]aminocarbonylamino}-α,D-5-epiglucofuranose (compound 4)

1,2-O-isopropylidene-3-O-dodecyl-5,6-dideoxy-5-N-{[4-chlorophenyl]aminocarbonylamino}α,D-5-epiglucofuranose (compound 5)

1,2-O-isopropylidene-3-O-decyl-5,6-dideoxy-5-N-{[4-chlorophenyl]aminocarbonylamino}α,D-5-epiglucofuranose (compound 6)

1,2-O-isopropylidene-3-O-heptyl-5,6-dideoxy-5-N-{[4-chlorophenyl]aminocarbonylamino}α,D-5-epiglucofuranose (compound 7)

1,2-O-isopropylidene-3-O-butyl-5,6-dideoxy-5-N-{[4-chlorophenyl]aminocarbonylamino}α,D-5-epiglucofuranose (compound 8)

1,2-O-isopropylidene-3-O-dodecyl-5,6-dideoxy-5-N-{[4-methoxyphenyl]aminocarbonylamino}α,D-5-epiglucofuranose (compound 9)

1,2-O-isopropylidene-3-O-decyl-5,6-dideoxy-5-N-{[4-methoxyphenyl]aminocarbonylamino}α,D-5-epiglucofuranose (compound 10)

1,2-O-isopropylidene-3-O-heptyl-5,6-dideoxy-5-N-{[4-methoxyphenyl]aminocarbonylamino}α,D-5-epiglucofuranose (compound 11)

1,2-O-isopropylidene-3-O-butyl-5,6-dideoxy-5-N-{[4-methoxyphenyl]aminocarbonylamino}α,D-5-epiglucofuranose (compound 12)

1,2-O-isopropylidene-3-O-dodecyl-5,6-dideoxy-5-N-{[4-tolyl]aminocarbonylamino}α,D-5-epiglucofuranose (compound 13)

1,2-O-isopropylidene-3-O-decyl-5,6-dideoxy-5-N-{[4-tolyl]aminocarbonylamino}α,D-5-epiglucofuranose (compound 14)

1,2-O-isopropylidene-3-O-heptyl-5,6-dideoxy-5-N-{[4-tolyl]aminocarbonylaminol}α,D-5-epiglucofuranose (compound 15)

1,2-O-isopropylidene-3-O-butyl-5,6-dideoxy-5-N-{[4-tolyl]aminocarbonylamino}α,D-5-epiglucofuranose (compound 16)

1,2-O-isopropylidene-3-O-dodecyl-5,6-dideoxy-5-N-{[4-(2-hydroxy-2-oxoethyl)phenyl]aminocarbonylamino}-α,D-5-epiallofuranose (compound 17)

1,2-O-isopropylidene-3-O-decyl-5,6-dideoxy-5-N-{[4-(2-hydroxy-2-oxoethyl)phenylaminocarbonylamino}-α,D-5-epiallofuranose (compound 18)

1,2-O-isopropylidene-3-O-heptyl-5,6-dideoxy-5-N-{[4-(2-hydroxy-2-oxoethyl)phenyl]aminocarbonylamino}-α,D-5-epiallofuranose (compound 19)

1,2-O-isopropylidene-3-O-butyl-5,6-dideoxy-5-N-{[4-(2-hydroxy-2-oxoethyl)phenyl]aminocarbonyl amino}-α,D-5-epiallofuranose (compound 20)

1,2-O-isopropylidene-3-O-dodecyl-5,6-dideoxy-5-N-{[4-chlorophenyl]aminocarbonylamino}α,D-5-epiallofuranose (compound 21)

1,2-O-isopropylidene-3-O-decyl-5,6-dideoxy-5-N-{[4-chlorophenyl]aminocarbonylamino}α,D-5-epiallofuranose (compound 22)

1,2-O-isopropylidene-3-O-heptyl-5,6-dideoxy-5-N-{[4-chlorophenyl]aminocarbonylaminol}α,D-5-epiallofuranose (compound 23)

1,2-O-isopropylidene-3-O-butyl-5,6-dideoxy-5-N-{[4-chlorophenyl]aminocarbonylamino}α,D-5-epiallofuranose (compound 24)

1,2-O-isopropylidene-3-O-dodecyl-5,6-dideoxy-5-N-{[4-methoxyphenyl]aminocarbonylamino}α,D-5-epiallofuranose (compound 25)

1,2-O-isopropylidene-3-O-decyl-5,6-dideoxy-5-N-{[4-methoxyphenyl]aminocarbonylamino}α,D-5-epiallofuranose (compound 26)

1,2-O-isopropylidene-3-O-heptyl-5,6-dideoxy-5-N-{[4-methoxyphenyl]aminocarbonylamino}α,D-5-epiallofuranose (compound 27)

1,2-O-isopropylidene-3-O-butyl-5,6-dideoxy-5-N-{[4-methoxyphenyl]aminocarbonylamino}α,D-5-epiallofuranose (compound 28)

1,2-O-isopropylidene-3-O-dodecyl-5,6-dideoxy-5-N-{[4-tolyl]aminocarbonylamino}α,D-5-epiallofuranose (compound 29)

1,2-O-isopropylidene-3-O-decyl-5,6-dideoxy-5-N-{[4-tolyl]aminocarbonylamino}α,D-5-epiallofuranose (compound 30)

1,2-O-isopropylidene-3-O-heptyl-5,6-dideoxy-5-N-{[4-tolyl]aminocarbonylamino}α,D-5-epiallofuranose (compound 31)

1,2-O-isopropylidene-3-O-butyl-5,6-dideoxy-5-N-{[4-tolyl]aminocarbonylamino}α,D-5-epiallofuranose (compound 32)

2,3-O-isopropylidene-1-O-butyl-5,6-dideoxy-5-N-{[4-(2-hydroxy-2-oxoethyl)phenyl]aminocarbonyl amino}-α,D-5-epimannofuranoside (compound 33)

2,3-O-isopropylidene-1-O-hexyl-5,6-dideoxy-5-N-{[4-(2-hydroxy-2-oxoethyl)phenyl]aminocarbonyl amino}-α,D-5-epimannofuranoside (compound 34)

2,3-O-isopropylidene-1-O-heptyl-5,6-dideoxy-5-N-{[4-(2-hydroxy-2-oxoethyl)phenyl]aminocarbonyl amino}-α,D-5-epimannofuranoside (compound 35)

2,3-O-isopropylidene-1-O-decyl-5,6-dideoxy-5-N-{[4-(2-hydroxy-2-oxoethyl)phenyl]aminocarbonyl amino}-α,D-5-epimannofuranoside (compound 36)

2,3-O-isopropylidene-1-O-dodecyl-5,6-dideoxy-5-N-{[4-(2-hydroxy-2-oxoethyl)phenyl]aminocarbonylamino}-α,D-5-epimannofuranoside (compound 37)

2,3-O-isopropylidene-1-O-butyl-5,6-dideoxy-5-N-{[4-chlorophenyl]aminocarbonylamino}-α,D-5-epimannofuranoside (compound 38)

2,3-O-isopropylidene-1-O-hexyl-5,6-dideoxy-5-N-{[4-chlorophenyl]aminocarbonylamino}-α,D-5-epimannofuranoside (compound 39)

2,3-O-isopropylidene-1-O-heptyl-5,6-dideoxy-5-N-{[4-chlorophenyl]aminocarbonylamino}-α,D-5-epimannofuranoside (compound 40)

2,3-O-isopropylidene-1-O-decyl-5,6-dideoxy-5-N-{[4-chlorophenyl]aminocarbonylamino}-α,D-5-epimannofuranoside (compound 41)

2,3-O-isopropylidene-1-O-dodecyl-5,6-dideoxy-5-N-{[4-chlorophenyl]aminocarbonylamino}-α,D-5-epimannofuranoside (compound 42)

2,3-O-isopropylidene-1-O-butyl-5,6-dideoxy-5-N-{[4-methoxyphenyl]aminocarbonylamino}-α,D-5-epimannofuranoside (compound 43)

2,3-O-isopropylidene-1-O-hexyl-5,6-dideoxy-5-N-{[4-methoxyphenyl]aminocarbonylamino}-α,D-5-epimannofuranoside (compound 44)

2,3-O-isopropylidene-1-O-heptyl-5,6-dideoxy-5-N-{[4-methoxyphenyl]aminocarbonylamino}-α,D-5-epimannofuranoside (compound 45)

2,3-O-isopropylidene-1-O-decyl-5,6-dideoxy-5-N-{[4-methoxyphenyl]aminocarbonylamino}-α,D-5-epimannofuranoside (compound 46)

2,3-O-isopropylidene-1-O-dodecyl-5,6-dideoxy-5-N-{[4-methoxyphenyl]aminocarbonylamino}-α,D-5-epimannofuranoside (compound 47)

2,3-O-isopropylidene-1-O-butyl-5,6-dideoxy-5-N-{[4-tolyl]aminocarbonylamino}-α,D-5-epimannofuranoside (compound 48)

2,3-O-isopropylidene-1-O-hexyl-5,6-dideoxy-5-N-{[4-tolyl]aminocarbonylamino}-α,D-5-epimannofuranoside (compound 49)

2,3-O-isopropylidene-1-O-heptyl-5,6-dideoxy-5-N-{[4-tolyl]aminocarbonylamino}-α,β-5-epimannofuranoside (compound 50)

2,3-O-isopropylidene-1-O-decyl-5,6-dideoxy-5-N-{[4-tolyl]aminocarbonylamino}-α,D-5-epimannofuranoside (compound 51)

2,3-O-isopropylidene-1-O-dodecyl-5,6-dideoxy-5-N-{[4-tolyl]aminocarbonylamino}α,D-5-epimannofuranoside (compound 52)

1,2-O-isopropylidene-3-O-dodecyl-5-deoxy-5-N-{[4-(2-hydroxy-2-oxoethyl)phenyl]aminocarbonylamino}-α,D-xylofuranose (compound 53)

1,2-O-isopropylidene-3-O-decyl-5-deoxy-5-N-{[4-(2-hydroxy-2-oxoethyl)phenyl]aminocarbonylamino}-α,D-xylofuranose (compound 54)

1,2-O-isopropylidene-3-O-hexyl-5-deoxy-5-N-{[4-(2-hydroxy-2-oxoethyl)phenyl]aminocarbonylamino}-α,D-xylofuranose (compound 55)

1,2-O-isopropylidene-3-O-butyl-5-deoxy-5-N-{[4-(2-hydroxy-2-oxoethyl)phenyl]aminocarbonylamino}-α,D-xylofuranose (compound 56)

1,2-O-isopropylidene-3-O-methyl-5-deoxy-5-N-{[4-(2-hydroxy-2-oxoethyl)phenyl]aminocarbonylamino}-α,D-xylofuranose (compound 57)

1,2-O-isopropylidene-3-O-dodecyl-5-deoxy-5-N-{[4-chlorophenyl]aminocarbonylamino}α,D-xylofuranose (compound 58)

1,2-O-isopropylidene-3-O-decyl-5-deoxy-5-N-{[4-chlorophenyl]aminocarbonylamino}α,D-xylofuranose (compound 59)

1,2-O-isopropylidene-3-O-hexyl-5-deoxy-5-N-{[4-chlorophenyl]aminocarbonylamino}α,D-xylofuranose (compound 60)

1,2-O-isopropylidene-3-O-butyl-5-deoxy-5-N-{[4-chlorophenyl]aminocarbonylamino}α,D-xylofuranose (compound 61)

1,2-O-isopropylidene-3-O-methyl-5-deoxy-5-N-{[4-chlorophenyl]aminocarbonylamino}α,D-xylofuranose (compound 62)

1,2-O-isopropylidene-3-O-dodecyl-5-deoxy-5-N-{[4-methoxyphenyl]aminocarbonylamino}α,D-xylofuranose (compound 63)

1,2-O-isopropylidene-3-O-decyl-5-deoxy-5-N-{[4-methoxyphenyl]aminocarbonylamino}α,D-xylofuranose (compound 64)

1,2-O-isopropylidene-3-O-hexyl-5-deoxy-5-N-{[4-methoxyphenyl]aminocarbonylamino}α,D-xylofuranose (compound 65)

1,2-O-isopropylidene-3-O-butyl-5-deoxy-5-N-{[4-methoxyphenyl]aminocarbonylamino}α,D-xylofuranose (compound 66)

1,2-O-isopropylidene-3-O-methyl-5-deoxy-5-N-{[4-methoxyphenyl]aminocarbonylamino}α,D-xylofuranose (compound 67)

1,2-O-isopropylidene-3-O-dodecyl-5-deoxy-5-N-{[4-tolyl]aminocarbonylamino}α,D-xylofuranose (compound 68)

1,2-O-isopropylidene-3-O-decyl-5-deoxy-5-N-{[4-tolyl]aminocarbonylamino}α,D-xylofuranose (compound 69)

1,2-O-isopropylidene-3-O-hexyl-5-deoxy-5-N-{[4-tolyl]aminocarbonylamino}α,D-xylofuranose (compound 70)

1,2-O-isopropylidene-3-O-butyl-5-deoxy-5-N-{[4-tolyl]aminocarbonylamino}α,D-xylofuranose (compound 71)

1,2-O-isopropylidene-3-O-methyl-5-deoxy-5-N-{[4-tolyl]aminocarbonylamino}α,D-xylofuranose (compound 72)

1,2-O-isopropylidene-3-O-dodecyl-5-deoxy-5-N-{[aminocarbonylamino]phenylacetyl-L-Leucyl-α,L-Aspartyl-L-Valyl-L-Proline}-α,D-xylofuranose (compound 73)

1,2-O-isopropylidene-3-O-dodecyl-5-deoxy-5-N-{[aminocarbonylamino]phenylacetyl-α,L-Aspartyl-L-Valyl-L-Proline}-α,D-xylofuranose (compound 74)

1,2-O-isopropylidene-3-O-dodecyl-5-deoxy-5-N-{[aminocarbonylamino]phenylacetyl-L-Valyl-L-Proline}-α,D-xylofuranose (compound 75)

1,2-O-isopropylidene-3-O-dodecyl-5-deoxy-5-N-{[4-(2-hydroxy-2-oxoethyl)phenyl]aminocarbonylamino}-α,D-ribofuranose (compound 76)

1,2-O-isopropylidene-3-O-decyl-5-deoxy-5-N-{[4-(2-hydroxy-2-oxoethyl)phenyl]aminocarbonylamino}-α,D-ribofuranose (compound 77)

1,2-O-isopropylidene-3-O-heptyl-5-deoxy-5-N-{[4-(2-hydroxy-2-oxoethyl)phenyl]aminocarbonylamino}-α,D-ribofuranose (compound 78)

1,2-O-isopropylidene-3-O-butyl-5-deoxy-5-N-{[4-(2-hydroxy-2-oxoethyl)phenyl]aminocarbonylamino}-α,D-ribofuranose (compound 79)

1,2-O-isopropylidene-3-O-methyl-5-deoxy-5-N-{[4-(2-hydroxy-2-oxoethyl)phenyl]aminocarbonylamino}-α,D-ribofuranose (compound 80)

1,2-O-isopropylidene-3-O-dodecyl-5-deoxy-5-N-{[4-chlorophenyl]aminocarbonylamino}α,D-ribofuranose (compound 81)

1,2-O-isopropylidene-3-O-decyl-5-deoxy-5-N-{[4-chlorophenyl]aminocarbonylamino)}α,D-ribofuranose (compound 82)

1,2-O-isopropylidene-3-O-heptyl-5-deoxy-5-N-{[4-chlorophenyl]aminocarbonylamino}α,D-ribofuranose (compound 83)

1,2-O-isopropylidene-3-O-butyl-5-deoxy-5-N-{[4-chlorophenyl]aminocarbonylamino)}α,D-ribofuranose (compound 84)

1,2-O-isopropylidene-3-O-methyl-5-deoxy-5-N-{[4-chlorophenyl]aminocarbonylamino}α,D-ribofuranose (compound 85)

1,2-O-isopropylidene-3-O-dodecyl-5-deoxy-5-N-{[4-methoxyphenyl]aminocarbonylamino}α,D-ribofuranose (compound 86)

1,2-O-isopropylidene-3-O-decyl-5-deoxy-5-N-{[4-methoxyphenyl]aminocarbonylamino}α,D-ribofuranose (compound 87)

1,2-O-isopropylidene-3-O-heptyl-5-deoxy-5-N-{[4-methoxyphenyl]aminocarbonylamino}α,D-ribofuranose (compound 88)

1,2-O-isopropylidene-3-O-butyl-5-deoxy-5-N-{[4-methoxyphenyl]aminocarbonylamino}α,D-ribofuranose (compound 89)

1,2-O-isopropylidene-3-O-methyl-5-deoxy-5-N-{[4-methoxyphenyl]aminocarbonylamino}α,D-ribofuranose (compound 90)

1,2-O-isopropylidene-3-O-dodecyl-5-deoxy-5-N-{[4-tolyl]aminocarbonylamino}α,D-ribofuranose (compound 91)

1,2-O-isopropylidene-3-O-decyl-5-deoxy-5-N-{[4-tolyl]aminocarbonylamino}α,D-ribofuranose (compound 92)

1,2-O-isopropylidene-3-O-heptyl-5-deoxy-5-N-{[4-tolyl]aminocarbonylamino}α,D-ribofuranose (compound 93)

1,2-O-isopropylidene-3-O-butyl-5-deoxy-5-N-{[4-tolyl]aminocarbonylamino}α,D-ribofuranose (compound 94)

1,2-O-isopropylidene-3-O-methyl-5-deoxy-5-N-{[4-tolyl]aminocarbonylamino}α,D-ribofuranose (compound 95)

1,2-O-isopropylidene-3-O-dodecyl-5-deoxy-5-N-{[aminocarbonylaminophenyl]acetyl-L-Leucyl-α,L-Aspartyl-L-Valyl-L-Proline}-α,D-ribofuranose (compound 96)

1,2-O-isopropylidene-3-O-dodecyl-5-deoxy-5-N-{[aminocarbonylaminophenyl]acetyl-α,L-Aspartyl-L-Valyl-L-Proline}-α,D-ribofuranose (compound 97)

1,2-O-isopropylidene-3-O-dodecyl-5-deoxy-5-N-{[aminocarbonylaminophenyl]acetyl-L-Valyl-L-Proline}-α,D-ribofuranose (compound 98)

2,3-O-isopropylidene-1-O-methyl-5-deoxy-5-N-{[4-(2-hydroxy-2-oxoethyl)phenyl]aminocarbonylamino}-α,D-lyxofuranoside (compound 99)

2,3-O-isopropylidene-1-O-butyl-5-deoxy-5-N-{[4-(2-hydroxy-2-oxoethyl)phenyl]aminocarbonylamino}-α,D-lyxofuranoside (compound 100)

2,3-O-isopropylidene-1-O-heptyl-5-deoxy-5-N-{[4-(2-hydroxy-2-oxoethyl)phenyl]aminocarbonylamino}-α,D-lyxofuranoside (compound 101)

2,3-O-isopropylidene-1-O-decyl-5-deoxy-5-N-{[4-(2-hydroxy-2-oxoethyl)phenyl]aminocarbonylamino}-α,D-lyxofuranose(compound 102)

2,3-O-isopropylidene-1-O-dodecyl-5-deoxy-5-N-{[4-(2-hydroxy-2-oxoethyl)phenyl]aminocarbonylamino)}-α,D-lyxofuranoside (compound 103)

2,3-O-isopropylidene-1-O-methyl-5-deoxy-5-N-{[4-chlorophenyl]aminocarbonylamino}α,D-lyxofuranoside (compound 104)

2,3-O-isopropylidene-1-O-butyl-5-deoxy-5-N-{[4-chlorophenyl]aminocarbonylamino}α,D-lyxofuranoside (compound 105)

2,3-O-isopropylidene-1-O-heptyl-5-deoxy-5-N-{[4-chlorophenyl]aminocarbonylamino}α,D-lyxofuranoside (compound 106)

2,3-O-isopropylidene-1-O-decyl-5-deoxy-5-N-{[4-chlorophenyl]aminocarbonylamino}α,D-lyxofuranoside (compound 107)

2,3-O-isopropylidene-1-O-dodecyl-5-deoxy-5-N-{[4-chlorophenyl]aminocarbonylamino}α,D-lyxofuranoside (compound 108)

2,3-O-isopropylidene-1-O-methyl-5-deoxy-5-N-{[4-methoxyphenyl]aminocarbonylamino}α,D-lyxofuranoside (compound 109)

2,3-O-isopropylidene-1-O-butyl-5-deoxy-5-N-{[4-methoxyphenyl]aminocarbonylamino}α,D-lyxofuranoside (compound 110)

2,3-O-isopropylidene-1-O-heptyl-5-deoxy-5-N-{[4-methoxyphenyl]aminocarbonylamino}α,D-lyxofuranoside (compound 111)

2,3-O-isopropylidene-1-O-decyl-5-deoxy-5-N-{[4-methoxyphenyl]aminocarbonylamino}α,D-lyxofuranoside (compound 112)

2,3-O-isopropylidene-1-O-dodecyl-5-deoxy-5-N-{[4-methoxyphenyl]aminocarbonylamino}α,D-lyxofuranoside (compound 113)

2,3-O-isopropylidene-1-O-methyl-5-deoxy-5-N-{[4-tolyl]aminocarbonylamino}α,D-lyxofuranoside (compound 114)

2,3-O-isopropylidene-1-O-butyl-5-deoxy-5-N-{[4-tolyl]aminocarbonylamino}α,D-lyxofuranoside (compound 115)

2,3-O-isopropylidene-1-O-heptyl-5-deoxy-5-N-{[4-tolyl]aminocarbonylamino}α,D-lyxofuranoside (compound 116)

2,3-O-isopropylidene-1-O-decyl-5-deoxy-5-N-{[4-tolyl]aminocarbonylamino}α,D-lyxofuranoside (compound 117)

2,3-O-isopropylidene-1-O-dodecyl-5-deoxy-5-N-{[4-tolyl]aminocarbonylamino}α,D-lyxofuranoside (compound 118)

2,3-O-isopropylidene-1-O-dodecyl-5-deoxy-5-N-{[aminocarbonylamino]phenylacetyl-L-Leucyl-α,L-Aspartyl-L-Valyl-L-Proline}-α,D-lyxofuranoside (compound 119)

2,3-O-isopropylidene-1-O-dodecyl-5-deoxy-5-N-{[aminocarbonylamino]phenylacetyl-α,L-Aspartyl-L-Valyl-L-Proline}-α,D-lyxofuranoside (compound 120) -α,D-lyxofuranoside (compound 120)

2,3-O-isopropylidene-1-O-dodecyl-5-deoxy-5-N-{[aminocarbonylamino]phenylacetyl-L-Valyl-L-Proline}-α,D-lyxofuranoside (compound 121)

2,3;4,6-Di-O-isopropylidene-1-carbonyl-L-Leucyl-α,L-Aspartyl-L-Valyl-LProline-α,L-xylo-2-hexulofuranosonic acid (compound 122)

2,3;4,6-Di-O-isopropylidene-1-carbonyl-α,L-Aspartyl-L-Valyl-LProline-α,L-xylo-2-hexulofuranosonic acid (compound 123)

2,3-O-isopropylidene-1-carbonyl-L-Leucyl-α,L-Aspartyl-L-Valyl-LProline-α,L-xylo-2-hexulofuranosonic acid (compound 124)

2,3-O-isopropylidene-1-carbonyl-α,L-Aspartyl-L-Valyl-L-Proline-α,L-xylo-2-hexulofuranosonic acid (compound 125)

2,3-O-isopropylidene-1-carbonyl-L-Valyl-L-Proline-α,L-xylo-2-hexulofuranosonic acid (compound 126)

2,3;4,6-Di-O-isopropylidene-1-deoxy-1-N-{[4-chlorophenyl]aminocarbonylamino}-α,L-xylo-2-hexulofuranose (compound 127)

2,3;4,6-Di-O-isopropylidene-1-deoxy-1-N-{[4-methoxyphenyl]aminocarbonylamino}-α,L-xylo-2-hexulofuranose (compound 128)

2,3;4,6-Di-O-isopropylidene-1-deoxy-1-N-{[4-tolyl]aminocarbonylamino}-α,L-xylo-2-hexulofuranose (compound 129)

2,3-O-isopropylidene-1-deoxy-1-N-{[4-(2-hydroxy-2oxoethyl))phenylaminocarbonylamino}-α,L-xylo-2-hexulofuranose (compound 130)

2,3-O-isopropylidene-1-deoxy-1-N-{[4-chlorophenyl]aminocarbonylamino}-α,L-xylo-2-hexulofuranose (compound 131)

2,3-O-isopropylidene-1-deoxy-1-N-{[4-methoxyphenyl]aminocarbonylamino}-α,L-xylo-2-hexulofuranose (compound 132)

2,3-O-isopropylidene-1-deoxy-1-N-{[4-tolyl]aminocarbonylamino}-α,L-xylo-2-hexulofuranose (compound 133)

2,3-O-isopropylidene-1deoxy-1-N-{[aminocarbonylaminophenylacetyl-L-Leucyl-α,L-Aspartyl-L-Valyl-L-Proline)}-α,L-xylo-2-hexulofuranose (compound 134)

2,3-O-isopropylidene-1-deoxy-1-N-{[aminocarbonylaminophenylacetyl-α,L-Aspartyl-L-Valyl-L-Proline)}-α,L-xylo-2-hexulofuranose (compound 135)

2,3-O-isopropylidene-1deoxy-1-N-{[aminocarbonylaminophenylacetyl-L-Valyl-L-Proline)}-α,L-xylo-2-hexulofuranose (compound 136).

The sugar derivatives of the present invention exhibit various pharmacological properties and are useful for treating animals with various inflammatory and autoimmune disorders, such as bronchial asthma, rheumatoid arthritis, type I diabetes, multiple sclerosis, allograft rejection, and psoriasis.

The free carboxylic acid groups contained in some of the compounds of the present invention are acidic and form organic and inorganic base salts. The resulting salts are useful by themselves and in the therapeutic composition. These salts may be prepared by the usual prior art techniques, such as suspending the compound in water and then adding one equivalent of the organic or inorganic base. Examples of suitable bases include TRIS, sodium, potassium, ammonium, etc.

The neutral solution of the resulting salt is subjected to rotary evaporation under diminished pressure to the volume necessary to ensure precipitation of the salt upon cooling, which is then filtered and dried. The salts of the present invention may also be prepared under strictly non-aqueous conditions. For example, dissolving free acid in a suitable organic solvent, adding exactly one equivalent of the desired base to the same solvent and stirring the solution at 0–5° C. causes the precipitation of the acid salt, which is then filtered, washed with the solvent, and dried.

Alternatively, the solvent is stripped off completely to obtain the desired salt. These salts are often preferred for use in formulating the therapeutic compositions of the invention because they are crystalline and relatively more stable and water-soluble. The salts are better adapted for parenteral administration than the free acids.

Because of their valuable pharmacological properties, the compounds of the present invention may be administered to an animal for treatment orally, topically, rectally, internasally, or by parenteral route. When the therapeutic composition is to be administered orally, it is preferred that the compounds of the present invention are admixed with a filler and/or binder, such as starch and a disintegrator. The admixture may be pressed into a tablet conveniently sized for oral administration. Capsules may also be filled with the powdered therapeutic composition for oral administration. Alternatively, a water solution of the amine salt or suspension of the therapeutic composition may be admixed with a flavored syrup and administered orally. A salt of the free acid is usually preferred when the compound is administered by parenteral route.

The pharmaceutical compositions of the present invention are preferably produced and administered in dosage units, each unit containing a certain amount of at least one compound of the invention and/or at least one physiologically acceptable base salt addition thereof. The dosage may be varied over extremely wide limits as the compounds are effective at low dosage levels and relatively free of toxicity. The compounds may be administered in the low micromolar concentration, which is therapeutically effective, and the dosage may be increased as desired up to the maximum dosage tolerated by the patient.

The present invention also includes within its scope prodrugs of the compounds of Formulae I, II and III. In general, such prodrugs will be functional derivatives of these compounds, which readily are converted in vivo into the defined compounds. Conventional procedures for the selection and preparation of suitable prodrugs are known.

The present invention also includes the enantiomers, diastereomers, N-oxides and pharmaceutically acceptable salts of these compounds as well as metabolites having the same type of activity. The present invention further includes pharmaceutical composition comprising the molecules of Formulae I, II and III or prodrugs, metabolite enantiomers, diastereomers, N-oxides, or pharmaceutically acceptable salts thereof, in combination with pharmaceutically acceptable carrier and optionally included excipient.

In the above synthesis, where specific acids, bases, solvents, catalysts, oxidising agents, reducing agents etc. are mentioned, it is to be understood that the other acids, bases, solvents, catalysts, oxidising agents, reducing agents etc., may be used. Similarly, the reaction temperature and duration of the reaction may be adjusted according to the need.

The examples mentioned below demonstrate the general synthetic procedure as well as the specific preparation of the preferred compound. The examples are provided to illustrate the details of the invention and should not be constrained to limit the scope of the present invention.

Experimental Details

Various solvents, such as acetone, methanol, pyridine, ether, tetrahydrofuran, hexanes, and dichloromethane, were dried using various drying reagents according to the procedure described in the literature. Wet solvents gave poor yields of the products and intermediates. IR spectra were recorded as nujol mulls or a thin neat film on a Perkin Elmer Paragon instrument. Nuclear Magnetic Resonance (NMR) data (H, C) were recorded on a Varian XL-300 MHz instrument using tetramethylsilane as an internal standard. Chemical Ionization Mass Spectra (CIMS) were obtained using a Finnigan MAT-4510 mass spectrometer equipped with an INCOS data system. Generally, a direct exposure probe and methane as the reagent gas (0.33 mm Hg, 120° C. source temperature) were used.

EXAMPLE 1

Preparation of 1,2-O-isopropylidene-3-O-decyl-5,6-dideoxy-5-N-{[4-(2-methoxy-2-oxoethyl)phenyl] aminocarbonylamino}-α,D-5-epiglucofuranose Step 1: 1,2-O-isopropylidene-3-O-decyl-6-deoxy-5-p-tosyl-α,D-glucofuranose 1,2-O-isopropylidene-3-O-decyl-6-deoxy-α,D-glucofuranose (11.0 gm) (prepared by the method reported in U.S. Pat. No. 5,360,792) was dissolved in pyridine (50 ml) and cooled to 0–5° C. To this was added p-toluenesulfonyl chloride (6.5 gm in 60 ml pyridine) dropwise under agitation. After 7 hours, the solvent was removed under vacuum. The residue that was obtained was extracted with ethyl acetate and washed with saturated sodium bicarbonate ($NaHCO_3$) solution and brine. The residue was then dried over anhydrous sodium sulphate ($Na_2SO_4$) and the solvent was removed under vacuum to obtain an oil, which was purified by column chromatography using an ethyl acetate-hexane mixture (10:90) as an eluent to obtain a yield of 82%.

The following compounds were prepared similarly to those described in Step 1:

1,2-O-isopropylidene-3-O-dodecyl-6-deoxy-5-p-tosyl-α-D-glucofuranose
1,2-O-isopropylidene-3-O-heptyl-6-deoxy-5-p-tosyl-α-D-glucofuranose
1,2-O-isopropylidene-3-O-butyl-6-deoxy-5-p-tosyl-α-D-glucofuranose
1,2-O-isopropylidene-3-O-methyl-6-deoxy-5-p-tosyl-α-D-glucofuranose.

Step 2: 1,2-O-isopropylidene-3-O-decyl-5,6-dideoxy-5-azido-α,D-5-epiglucofuranose A mixture of the compound obtained from Step 1 (12.0 gm), $NaN_3$ (12.0 gm), and N,N-dimethylformamide (DMF) (50 ml) was heated at 100° C. for 48 hours, after which the solvent was evaporated off under vacuum. The residue that was obtained was dissolved in ethyl acetate and washed with water (2 times 50 ml). The organic layer was dried over anhydrous $Na_2SO_4$ and the solvent was removed under vacuum. The crude material was purified by column chromatography over silica gel (100–200 mesh) using an ethyl acetate-hexane mixture (2:98) as an eluent to obtain an oil in 90% yield.

The following compounds were prepared similarly:

1,2-O-isopropylidene-3-O-dodecyl-5,6-dideoxy-5-azido-α,D-5-epiglucofuranose
1,2-O-isopropylidene-3-O-heptyl-5,6-dideoxy-5-azido-α,D-5-epiglucofuranose
1,2-O-isopropylidene-3-O-butyl-5,6-dideoxy-5-azido-α,D-5-epiglucofuranose
1,2-O-isopropylidene-3-O-methyl-5,6-dideoxy-5-azido-α,D-5-epiglucofuranose.

Step 3: 1,2-O-isopropylidene-3-O-decyl-5,6-dideoxy-5-amino-α,D-5-epiglucofuranose To a suspension of LAH (2.0 gm) in dry tetrahydrofuran (THF) (50 ml) at 0–5° C. was added the solution of the above compound (8.0 gm in 20 ml of THF) dropwise. Once the addition was complete, the reaction was stirred at room temperature for 2 hours. Excess LAH was decomposed by the addition of an ice-water mixture. The reaction mixture was then filtered through celite, washed with salt with 100 ml of THF and the solvent removed under vacuum. The residue was dissolved in 200 ml of ethyl acetate and washed with water and brine. The solvent was dried over anhydrous $Na_2SO_4$ and removed under vacuum to obtain an oil in 91% yield. The compound showed a single spot on thin layer chromatography (TLC) and was used as such for the next step.

The following compounds were prepared similarly:

1,2-O-isopropylidene-3-O-dodecyl-5,6-dideoxy-5-amino-α, D-5-epiglucofuranose
1,2-O-isopropylidene-3-O-heptyl-5,6-dideoxy-5-amino-α, D-5-epiglucofuranose
1,2-O-isopropylidene-3-O-butyl-5,6-dideoxy-5-amino-α,D-5-epiglucofuranose
1,2-O-isopropylidene-3-O-methyl-5,6-dideoxy-5-amino-α, D-5-epiglucofuranose.

Step 4: 1,2-O-isopropylidene-3-O-decyl-5,6-dideoxy-5-N-{[4-(2-methoxy-2-oxoethyl)phenyl]aminocarbonylamino}-α,D-5-epiglucofuranose To a cold solution of amine (1.0 gm) in dry methyl chloride ($CH_2Cl_2$)(10 ml) was added the methyl ester of p-isocyanate-4-phenyl acetic acid (0.56 gm) in 20 ml of dry $CH_2Cl_2$ at 0–5° C. The reaction was stirred at the same temperature for 3 hours, after which 90 ml more of $CH_2Cl_2$ were added to it. It was then washed with water (2 times 10 ml) and brine (2 times 10 ml), dried over anhydrous $Na_2SO_4$, and the solvent was removed under vacuum to obtain an oil. The product was purified by flash column chromatography (230–400 mesh) and eluted with an ethyl acetate-hexane mixture (20:80) to obtain a white solid in 77% yield of the pure product.

The following compounds were prepared similarly to those described in Example 1, Step 4:

1,2-O-isopropylidene-3-O-dodecyl-5,6-dideoxy-5-N-{[4-(2-methoxy-2-oxoethyl)phenyl]aminocarbonylamino}-α, D-5-epiglucofuranose
1,2-O-isopropylidene-3-O-heptyl-5,6-dideoxy-5-N-{[4-(2-methoxy-2-oxoethyl)phenyl]aminocarbonylamino}-α,D-5-epiglucofuranose
1,2-O-isopropylidene-3-O-butyl-5,6-dideoxy-5-N-{[4-(2-methoxy-2-oxoethyl)phenyl]aminocarbonylamino}-α,D-5-epiglucofuranose
1,2-O-isopropylidene-3-O-methyl-5,6-dideoxy-5-N-{[4-(2-methoxy-2-oxoethyl)phenyl]aminocarbonylamino}-α,D-5-epiglucofuranose.

EXAMPLE 2

Preparation of 1,2-O-isopropylidene-3-O-decyl-5,6-dideoxy-5-N-{[4-(2-hydroxy-2-oxoethyl)phenyl]aminocarbonylamino}-α,D-5-epiglucofuranose A mixture of ester as obtained in Example 1, Step 4 (1.0 gm) and aqueous NaOH (1N, 30 ml) was heated at 50° C. for two hours. The reaction was cooled in an ice-batch and acidified to pH 3 with 3N hydrochloric acid (HCl). A white solid separated, which became oil upon standing at room temperature. This product was extracted with ethyl acetate and washed with water, dried over anhydrous $Na_2SO_4$ and the solvent was removed under vacuum to obtain an oil. The crude product was purified by flash column chromatography by eluting with an ethyl acetate-hexane mixture (35:65) to obtain an oil in 92.5% yield.

The following compounds were prepared similarly:

1,2-O-isopropylidene-3-O-dodecyl-5,6-dideoxy-5-N-{[4-(2-hydroxy-2-oxoethyl)phenyl]aminocarbonylamino}-α, D-5-epiglucofuranose
1,2-O-isopropylidene-3-O-heptyl-5,6-dideoxy-5-N-{[4-(2-hydroxy-2-oxoethyl)phenyl]aminocarbonylamino}-α,D-5-epiglucofuranose
1,2-O-isopropylidene-3-O-butyl-5,6-dideoxy-5-N-{[4-(2-hydroxy-2-oxoethyl)phenyl]aminocarbonylamino}-α,D-5-epiglucofuranose
1,2-O-isopropylidene-3-O-methyl-5,6-dideoxy-5-N-{[4-(2-hydroxy-2-oxoethyl)phenyl]aminocarbonylamino}-α,D-5-epiglucofuranose.

EXAMPLE 3

Preparation of 1,2-O-isopropylidene-3-O-alkyl or alkylaryl-5,6-dideoxy-5-N-{[4-(chloro, methyl or methoxy)-phenyl]aminocarbonylamino}-α,D-5-epiglucofuranose The desired amine, prepared similarly as described in Example 1, Step 3, was reacted with an appropriate isocyanate, using the same procedure as described in Example 1, Step 4, to obtain the desired compound.

The following compounds were prepared similarly:

1,2-O-isopropylidene-3-O-dodecyl-5,6-dideoxy-5-N-{[4-chlorophenyl]aminocarbonylamino}α,D-5-epiglucofuranose
1,2-O-isopropylidene-3-O-decyl-5,6-dideoxy-5-N-{[4-chlorophenyl]aminocarbonylamino α,D-5-epiglucofuranose
1,2-O-isopropylidene-3-O-heptyl-5,6-dideoxy-5-N-{[4-chlorophenyl]aminocarbonylamino}α,D-5-epiglucofuranose
1,2-O-isopropylidene-3-O-butyl-5,6-dideoxy-5-N-{[4-chlorophenyl]aminocarbonylamino}α,D-5-epiglucofuranose
1,2-O-isopropylidene-3-O-dodecyl-5,6-dideoxy-5-N-{[4-methoxyphenyl]aminocarbonylamino}α,D-5-epiglucofuranose
1,2-O-isopropylidene-3-O-decyl-5,6-dideoxy-5-N-{[4-methoxyphenyl]aminocarbonyl amino}α,D-5-epiglucofuranose
1,2-O-isopropylidene-3-O-heptyl-5,6-dideoxy-5-N-{[4-methoxyphenyl]aminocarbonylamino}α,D-5-epiglucofuranose
1,2-O-isopropylidene-3-O-butyl-5,6-dideoxy-5-N-{[4-methoxyphenyl]aminocarbonylamino}α,D-5-epiglucofuranose
1,2-O-isopropylidene-3-O-dodecyl-5,6-dideoxy-5-N-{[4-tolyl]aminocarbonylamino}α,D-5-epiglucofuranose
1,2-O-isopropylidene-3-O-decyl-5,6-dideoxy-5-N-{[4-tolyl]aminocarbonylamino}α,D-5-epiglucofuranose
1,2-O-isopropylidene-3-O-heptyl-5,6-dideoxy-5-N-{[4-tolyl]aminocarbonylamino}α,D-5-epiglucofuranose
1,2-O-isopropylidene-3-O-butyl-5,6-dideoxy-5-N-{[4-tolyl]aminocarbonylamino}α,D-5-epiglucofuranose.

EXAMPLE 4

Preparation of 1,2-O-isopropylidene-3-O-dodecyl-5,6-dideoxy-5-N-{[4-(2-methoxy-2-oxoethyl)phenyl]aminocarbonylamino}-α,D-5-epiallofuranose Step 1: 1,2-O-isopropylidene-3-O-dodecyl-6-deoxy-5-p-tosyl-60,D-allofuranose 1,2-O-isopropylidene-3-O-dodecyl-6-deoxy-α,D-allofuranose (prepared by the method reported in U.S. Pat. No. 4,996,195) was reacted with p-toluenesulfonyl chloride, using the procedure described in Example 1, Step 1, to obtain the desired compound in 86% yield.

The following compounds were prepared similarly to those described in Example 4, Step 1:

1,2-O-isopropylidene-3-O-decyl-6-deoxy-5-p-tosyl-α,D-allofuranose
1,2-O-isopropylidene-3-O-heptyl-6-deoxy-5-p-tosyl-α,D-allofuranose
1,2-O-isopropylidene-3-O-butyl-6-deoxy-5-p-tosyl-α,D-allofuranose.

Step 2: 1,2-O-isopropylidene-3-O-dodecyl-5,6-dideoxy-5-azido-α,D-5-epiallofuranose A mixture of the above tosylate, NaN$_3$, and DMF was heated at 100° C., using the same procedure described in Example 1, Step 2, to obtain the desired compound in 82% yield.

The compounds prepared similarly were as follows:

1,2-O-isopropylidene-3-O-decyl-5,6-dideoxy-5-azido-α,D-5-epiallofuranose
1,2-O-isopropylidene-3-O-heptyl-5,6-dideoxy-5-azido-α,D-5-epiallofuranose
1,2-O-isopropylidene-3-O-butyl-5,6-dideoxy-5-azido-α,D-5-epiallofuranose.

Step 3: 1,2-O-isopropylidene-3-O-dodecyl-5,6-dideoxy-5-amino-α,D-5-epiallofuranose This compound was prepared (90% yield) by hydrogenating the above azide with LAH following the procedure described in Example 1, Step 3.

The following compounds were prepared similarly:

1,2-O-isopropylidene-3-O-decyl-5,6-dideoxy-5-amino-α,D-5-epiallofuranose
1,2-O-isopropylidene-3-O-heptyl-5,6-dideoxy-5-amino-α,D-5-epiallofuranose
1,2-O-isopropylidene-3-O-butyl-5,6-dideoxy-5-amino-α,D-5-epiallofuranose.

Step 4: 1,2-O-isopropylidene-3-O-dodecyl-5,6-dideoxy-5-N-{[4-(2-methoxy-2-oxoethyl)phenyl]aminocarbonylamino}-α,D-5-epiallofuranose The amine obtained in Step 3 was reacted with methyl ester of p-isocyanate-4-phenylacetic acid, using the method described in Example 1, Step 4, to obtain the desired ureido compound in 79% yield.

The following compounds were prepared similarly to those described in Example 4, Step 4:

1,2-O-isopropylidene-3-O-decyl-5,6-dideoxy-5-N-{[4-(2-methoxy-2-oxoethyl)phenyl]aminocarbonylamino}-α,D-5-epiallofuranose
1,2-O-isopropylidene-3-O-heptyl-5,6-dideoxy-5-N-{[4-(2-methoxy-2-oxoethyl)phenyl]aminocarbonylamino}-α,D-5-epiallofuranose
1,2-O-isopropylidene-3-O-butyl-5,6-dideoxy-5-N-{[4-(2-methoxy-2-oxoethyl)phenyl]aminocarbonylamino}-α,D-5-epiallofuranose.

EXAMPLE 5

Preparation of 1,2-O-isopropylidene-3-O-dodecyl-5,6-dideoxy-5-N-{[4-(2-hydroxy-2-oxoethyl)phenyl]aminocarbonylamino}-α,D-5-epiallofuranose The ester obtained in Example 4, Step 4 was hydrolyzed with aqueous NaOH (1N) using the procedure outlined in Example 2. The yield of the pure product was 64%.

The following compounds were prepared similarly:

1,2-O-isopropylidene-3-O-decyl-5,6-dideoxy-5-N-{[4-(2-hydroxy-2-oxoethyl)phenylaminocarbonylamino}-α,D-5-epiallofuranose
1,2-O-isopropylidene-3-O-heptyl-5,6-dideoxy-5-N-{[4-(2-hydroxy-2-oxoethyl)phenyl]aminocarbonylamino}-α,D-5-epiallofuranose
1,2-O-isopropylidene-3-O-butyl-5,6-dideoxy-5-N-{[4-(2-hydroxy-2-oxoethyl)phenyl]aminocarbonylamino}-α,D-5-epiallofuranose.

EXAMPLE 6

Preparation of 1,2-O-isopropylidene-3-O-alkyl or alkylaryl-5,6-dideoxy-5-N-{[4-(chloro,methyl or methoxy)-phenyl]aminocarbonylamino}-α,D-5-epiallofuranose The desired amine, prepared similarly to that described in Example 4, Step 3, was reacted with an appropriate isocyanate, using the procedure described in Example 1, Step 4, to obtain the desired compound in 81% yield.

The following compounds were prepared similarly:

1,2-O-isopropylidene-3-O-dodecyl-5,6-dideoxy-5-N-{[4-chlorophenyl]aminocarbonylamino}α,D-5-epiallofuranose
1,2-O-isopropylidene-3-O-decyl-5,6-dideoxy-5-N-{[4-chlorophenyl]aminocarbonylamino}α,D-5-epiallofuranose
1,2-O-isopropylidene-3-O-heptyl-5,6-dideoxy-5-N-{[4-chlorophenyl]aminocarbonylamino}α,D-5-epiallofuranose
1,2-O-isopropylidene-3-O-butyl-5,6-dideoxy-5-N-{[4-chlorophenyl]aminocarbonylamino}α,D-5-epiallofuranose
1,2-O-isopropylidene-3-O-dodecyl-5,6-dideoxy-5-N-{[4-methoxyphenyl]aminocarbonylamino}α,D-5-epiallofuranose
1,2-O-isopropylidene-3-O-decyl-5,6-dideoxy-5-N-{[4-methoxyphenyl]aminocarbonylamino}α,D-5-epiallofuranose
1,2-O-isopropylidene-3-O-heptyl-5,6-dideoxy-5-N-{[4-methoxyphenyl]aminocarbonylamino}α,D-5-epiallofuranose
1,2-O-isopropylidene-3-O-butyl-5,6-dideoxy-5-N-{[4-methoxyphenyl]aminocarbonylamino}α,D-5-epiallofuranose
1,2-O-isopropylidene-3-O-dodecyl-5,6-dideoxy-5-N-{[4-tolyl]aminocarbonylamino}α,D-5-epiallofuranose
1,2-O-isopropylidene-3-O-decyl-5,6-dideoxy-5-N-{[4-tolyl]aminocarbonylamino}α,D-5-epiallofuranose
1,2-O-isopropylidene-3-O-heptyl-5,6-dideoxy-5-N-{[4-tolyl]aminocarbonylamino}α,D-5-epiallofuranose
1,2-O-isopropylidene-3-O-butyl-5,6-dideoxy-5-N-{[4-tolyl]aminocarbonylamino}α,D-5-epiallofuranose.

EXAMPLE 7

Preparation of 2,3-O-isopropylidene-1-O-dodecyl-5,6-dideoxy-5-N-{[4-(2-methoxy-2-oxoethyl)phenyl]aminocarbonylamino-α,D-5-epimannofuranoside Step 1: 2,3-O-isopropylidene-1-O-dodecyl-6-deoxy-5-p-tosyl-α,D-mannofuranoside 2,3-O-isopropylidene-1-O-dodecyl-6-deoxy-(α,D-mannofuranoside (prepared to the method reported in U.S.

Pat. No. 5,360,794)(6.0 gm) was dissolved in pyridine (5 ml) and cooled to 0–5° C. To this, p-toluenesulfonyl chloride (5.3 gm) was added portionwise with stirring. After 7 hours, the solvent was removed under high vacuum pump. The residue obtained was extracted with ethyl acetate, washed with saturated NaHCO$_3$ solution (2 times 10 ml) and brine (2 times 10 ml), and dried over anhydrous Na$_2$SO$_4$. The solvent was removed under vacuum to obtain an oil, which was purified by column chromatography and eluted with an ethyl acetate-hexane mixture (5:95) to obtain the desired compound in 82% yield.

The compounds prepared similarly were as follows:

2,3-O-isopropylidene-1-O-butyl-6-deoxy-5-p-tosyl-α,D-mannofuranoside
2,3-O-isopropylidene-1-O-hexyl-6-deoxy-5-p-tosyl-α,D-mannofuranoside
2,3-O-isopropylidene-1-O-heptyl-6-deoxy-5-p-tosyl-α,D-mannofuranoside
2,3-O-isopropylidene-1-O-decyl-6-deoxy-5-p-tosyl-α,D-mannofuranoside.

Step 2: 2,3-O-isopropylidene-1-O-dodecyl-5,6-dideoxy-5-azido-α,D-5-epimannofuranoside A mixture of the above compound (9.0 gm), NaN$_3$ (9.0 gm), and DMF (50 ml) was heated at 100° C. for 48 hours. The solvent was then removed under vacuum and the residue obtained was dissolved in ethyl acetate and washed with water (2 times 50 ml). The residue was dried over anhydrous Na$_2$SO$_4$ and the solvent was removed under vacuum. The crude material was purified by column chromatography (silica gel 100–200 mesh) on eluting with a mixture of 2% ethyl acetate in hexane to obtain an oil in 42% yield.

The following compounds were prepared similarly:

2,3-O-isopropylidene-1-O-butyl-5,6-dideoxy-5-azido-α,D-5-epimannofuranoside
2,3-O-isopropylidene-1-O-hexyl-5,6-dideoxy-5-azido-α,D-5-epimannofuranoside
2,3-O-isopropylidene-1-O-heptyl-5,6-dideoxy-5-azido-α,D-5-epimannofuranoside
2,3-O-isopropylidene-1-O-decyl-5,6-dideoxy-5-azido-α,D-5-epimannofuranoside.

Step 3: 2,3-O-isopropylidene-1-O-dodecyl-5,6-dideoxy-5-amino-α,D-5-epimannofuranoside To a suspension of LAH (2.0 gm) in dry THF (50 ml) at 0–5° C. was added a solution of the compound obtained in Step 3 (3.0 gm in 10 ml of THF) dropwise. Once the addition was complete, the reaction was stirred at room temperature for 2 hours. Excess LAH was decomposed by the addition of ice-water mixture. The reaction mixture was then filtered through celite, washed with 100 ml of THF, and the solvent was removed under vacuum. The residue was dissolved in 200 ml of ethyl acetate and washed with water and brine. The solvent was dried over anhydrous Na$_2$SO$_4$ and removed under vacuum. Crude product was purified by column chromatography and eluted with an ethyl acetate-hexane mixture (50:50) to obtain a 61% yield of the pure product.

The following compounds were prepared similarly:

2,3-O-isopropylidene-1-O-butyl-5,6-dideoxy-5-amino-α,D-5-epimannofuranoside
2,3-O-isopropylidene-1-O-hexyl-5,6-dideoxy-5-amino-α,D-5-epimannofuranoside
2,3-O-isopropylidene-1-O-heptyl-5,6-dideoxy-5-amino-α,D-5-epimannofuranoside
2,3-O-isopropylidene-1-O-decyl-5,6-dideoxy-5-amino-α,D-5-epimannofuranoside.

Step 4: 2,3-O-isopropylidene-1-O-dodecyl-5,6-dideoxy-5-N-{[4-(2-methoxy-2-oxo-ethyl)phenyl]aminocarbonylamino}-α,D-5-epimannofuranoside To a cold solution of amine (0.5 gm) in dry CH$_2$Cl$_2$ (10 ml) was added the methyl ester of p-isocyanate-4-phenyl acetic acid (250 mg) in 5 ml of dry CH$_2$Cl$_2$ at 0–5° C. The reaction mixture was stirred at the sample temperature for 3 hours, after which 90 ml more of CH$_2$Cl$_2$ was added to it. It was then washed with water (2 times 10 ml) and brine (2 times 10 ml), dried over anhydrous Na$_2$SO$_4$, and the solvent was removed under vacuum to obtain an oil. The product was purified by column chromatography (230–400 mesh) and eluted with an ethyl acetate-hexane mixture (20:80) to obtain a white solid in 80% yield.

The following compounds were prepared similarly:

2,3-O-isopropylidene-1-O-butyl-5,6-dideoxy-5-N-{[4-(2-methoxy-2-oxoethyl)phenyl]aminocarbonyl amino}-α,D-5-epimannofuranoside
2,3-O-isopropylidene-1-O-hexyl-5,6-dideoxy-5-N-{[4-(2-methoxy-2-oxoethyl)phenyl]aminocarbonyl amino}-α,D-5-epimannofuranoside
2,3-O-isopropylidene-1-O-heptyl-5,6-dideoxy-5-N-{[4-(2-methoxy-2-oxoethyl)phenyl]aminocarbonyl amino}-α,D-5-epimannofuranoside
2,3-O-isopropylidene-1-O-heptyl-5,6-dideoxy-5-N-{[4-(2-methoxy-2-oxoethyl)phenyl]aminocarbonyl amino}-α,D-5-epimannofuranoside

EXAMPLE 8

Preparation of 2,3-O-isopropylidene-1-O-dodecyl-5,6-dideoxy-5-N-{[4-(2-hydroxy-2-oxoethyl)phenyl]aminocarbonylamino}-α,D-5-epimannofuranoside A mixture of ester (0.3 gm), as obtained in Example 7, Step 4,and 10 ml of aqueous NaOH (1N) was heated at 50° C. for 2 hours. Thereafter, the reaction was cooled in an ice-batch and acidified to pH 3 with 3N HCl and a white solid separated, which became oil upon standing at room temperature. This product was extracted with ethyl acetate and washed with water, dried over anhydrous Na$_2$SO$_4$, and the solvent was removed under vacuum to obtain the oil. Crude product was purified by flash column chromatography by eluting with an ethyl acetate-hexane mixture (35:65) to obtain a low melting solid in 71% yield.

The following compounds were prepared similarly:

2,3-O-isopropylidene-1-O-butyl-5,6-dideoxy-5-N-{[4-(2-hydroxy-2-oxoethyl)phenyl]aminocarbonyl amino}-α,D-5-epimannofuranoside
2,3-O-isopropylidene-1-O-hexyl-5,6-dideoxy-5-N-{[4-(2-hydroxy-2-oxoethyl)phenyl]aminocarbonyl amino}-α,D-5-epimannofuranoside
2,3-O-isopropylidene-1-O-heptyl-5,6-dideoxy-5-N-{[4-(2-hydroxy-2-oxoethyl)phenyl]aminocarbonyl amino}-α,D-5-epimannofuranoside
2,3-O-isopropylidene-1-O-decyl-5,6-dideoxy-5-N-{[4-(2-hydroxy-2-oxoethyl)phenyl]aminocarbonyl amino}-α,D-5-epimannofuranoside.

EXAMPLE 9

Preparation of 2,3-O-isopropylidene-1-O-alkyl or alkylaryl-5,6-dideoxy-5-N-{[4-(chloro, methyl or methoxy)-phenyl]aminocarbonylamino}-α,D-5-epimannofuranoside The desired amine, prepared similarly to that described in Example 7, Step 3, was reacted with an appropriate isocyanate, using the same procedure described in Example 7, Step 4, to obtain the desired compound.

The following compounds were prepared similarly:

2,3-O-isopropylidene-1-O-butyl-5,6-dideoxy-5-N-{[4-chlorophenyl]aminocarbonylamino}-α,D-5-epimannofuranoside
2,3-O-isopropylidene-1-O-hexyl-5,6-dideoxy-5-N-{[4-chlorophenyl]aminocarbonylamino}-α,D-5-epimannofuranoside
2,3-O-isopropylidene-1-O-heptyl-5,6-dideoxy-5-N-{[4-chlorophenyl]aminocarbonylamino}-α,D-5-epimannofuranoside
2,3-O-isopropylidene-1-O-decyl-5,6-dideoxy-5-N-{[4-chlorophenyl]aminocarbonylamino}-α,D-5-epimannofuranoside
2,3-O-isopropylidene-1-O-dodecyl-5,6-dideoxy-5-N-{[4-chlorophenyl]aminocarbonylamino}-α,D-5-epimannofuranoside
2,3-O-isopropylidene-1-O-butyl-5,6-dideoxy-5-N-{[4-chlorophenyl]aminocarbonylamino}-α,D-5-epimannofuranoside
-2,3-O-isopropylidene-1-O-hexyl-5,6-dideoxy-5-N-{[4-methoxyphenyl]aminocarbonylamino}α,D-5-epimannofuranoside
2,3-O-isopropylidene-1-O-heptyl-5,6-dideoxy-5-N-{[4-methoxyphenyl]aminocarbonylamino}-α,D-5-epimannofuranoside
2,3-O-isopropylidene-1-O-decyl-5,6-dideoxy-5-N-{[4-methoxyphenyl]aminocarbonylamino}-α,D-5-epimannofuranoside
2,3-O-isopropylidene-1-O-dodecyl-5,6-dideoxy-5-N-{[4-methoxyphenyl]aminocarbonylamino}-α,D-5-epimannofuranoside
2,3-O-isopropylidene-1-O-butyl-5,6-dideoxy-5-N-{[4-tolyl]aminocarbonylamino}-α,D-5-epimannofuranoside
2,3-O-isopropylidene-1-O-hexyl-5,6-dideoxy-5-N-{[4-tolyl]aminocarbonylamino}-α,D-5-epimannofuranoside
2,3-O-isopropylidene-1-O-heptyl-5,6-dideoxy-5-N-{[4-tolyl]aminocarbonylamino}-α,D-5-epimannofuranoside
2,3-O-isopropylidene-1-O-decyl-5,6-dideoxy-5-N-{[4-tolyl]aminocarbonylamino}-α,D-5-epimannofuranoside
-2,3-O-isopropylidene-1-O-dodecyl-5,6-dideoxy-5-N-{[4-tolyl]aminocarbonylamino}-α,D-5-epimannofuranoside.

EXAMPLE 10

Preparation of 1,2-O-isopropylidene-3-O-dodecyl-5-deoxy-5-N-{[4-(2-methoxy-2-oxoethyl)phenyl]aminocarbonylamino}-α,D-xylofuranose Step 1: 1,2-O-isopropylidene-3-O-dodecyl-4-carboxaldehyde-α,D-glucofuranose To a suspension of 1,2-O-isopropylidene-3-O-dodecyl-α, D-gucofuranose (20.0 gm) (prepared by the method reported in U.S. Pat. No. 5,360,792) in water (20 ml) at 0–5° C., a solution of NaIO₄ (20.0 gm in 60 ml of water) was added dropwise, after which the reaction was stirred at room temperature for 10 hours. 250 ml of ethanol was added to the reaction mixture and a white solid was separated, which was filtered out. Solvent was evaporated from the filtrate under vacuum and ethyl acetate was added to the residue. It was then washed with water, dried over anhydrous Na₂SO₄, and the solvent was removed under vacuum to obtain an oil in 81% yield. Product was used as such without any purification for the next step.

The following compounds were prepared similarly:

1,2-O-isopropylidene-3-O-methyl-4-carboxaldehyde-α,D-glucofuranose
1,2-O-isopropylidene-3-O-butyl-4-carboxaldehyde-α,D-glucofuranose
1,2-O-isopropylidene-3-O-hexyl-4-carboxaldehyde-α,D-glucofuranose
1,2-O-isopropylidene-3-O-decyl-4-carboxaldehyde-α,D-glucofuranose.

Step 2: 1,2-O-isopropylidene-3-O-dodecyl-4-oximino-α,D-glucofuranose

To a solution of hydroxylamine hydrochloride (12 gm) in a mixture of pyridine (50 ml) at room temperature was added a solution of aldehyde (obtained in Step 1, 15 gm in 30 ml ethanol) and heated at 75° C. for 24 hours. Pyridine was removed under high vacuum pump, water was added to it, and the desired compound was extracted with ethyl acetate. The ethyl acetate layer was washed with water, dried over anhydrous Na₂SO₄, and the solvent was removed under vacuum. The crude product so obtained was purified using flash chromatography by eluting with a 15:85 ethyl acetate-hexane mixture to obtain the pure product in 90% yield.

The following compounds were prepared similarly:

1,2-O-isopropylidene-3-O-methyl-4-oximino-α,D-glucofuranose
1,2-O-isopropylidene-3-O-butyl-4-oximino-α,D-glucofuranose
1,2-O-isopropylidene-3-O-hexyl-4-oximino-α,D-glucofuranose
1,2-O-isopropylidene-3-O-decyl-4-oximino-α,D-glucofuranose.

Step 3: 1,2-O-isopropylidene-3-O-dodecyl-5-deoxy-5-amino-α,D-xylofuranose.

To a suspension of LAH (6 gm) in dry THF (50 ml) at 0–5° C. was added a solution of oxime obtained in Step 2 (16 gm dissolved in 80 ml of THF) dropwise. Once the addition was over, the reaction mixture was stirred at room temperature for 4 hours. Excess LAH was decomposed by the addition of ice-water mixture. The reaction mixture was then filtered through celite, washed with 100 ml of THF and the solvent was removed under vacuum. The residue was dissolved in 200 ml of ethyl acetate, washed with water and brine. The solvent was dried over anhydrous Na₂SO₄ and removed under vacuum to obtain an oil, which was purified by column chromatography by eluting with ethyl acetate to obtain the viscous oil in 68% yield.

The following compounds were prepared similarly:

1,2-O-isopropylidene-3-O-methyl-5-deoxy-5-amino-α,D-xylofuranose
1,2-O-isopropylidene-3-O-butyl-5-deoxy-5-amino-α,D-xylofuranose
1,2-O-isopropylidene-3-O-hexyl-5-deoxy-5-amino-α,D-xylofuranose
1,2-O-isopropylidene-3-O-decyl-5-deoxy-5-amino-α,D-xylofuranose.

Step 4: 2-O-isopropylidene-3-O-dodecyl-5-deoxy-5-N-{[4-(2-methoxy-2-oxoethyl)phen-yl aminocarbonylamino}-α,D-xylofuranose To a cold solution of amine (2.4 gm, 8.12 mmol) in dry CH₂Cl₂ (10 ml) was added a solution of methyl ester of p-isocyanate-4-phenyl acetic acid (1.5 gm, 8.12 mmol) in 5 ml of dry CH$_2$Cl$_2$ at 0–5° C. and the reaction was stirred at the same temperature for 3 hours. 90 ml more of CH$_2$Cl$_2$ were added to the solution, which was washed with water (2 times 10 ml) and brine (2 times 10 ml), dried over anhydrous Na$_2$SO$_4$, and the solvent was removed under vacuum to obtain an oil. The product was purified by flash column chromatography and eluted with an ethyl acetate-hexane mixture (20:80) to obtain a white solid in 63% yield, m. p. 74–75° C.

The following compounds were prepared similarly to those described in Example 10, Step 4:

1,2-O-isopropylidene-3-O-decyl-5-deoxy-5-N-{[4-(2-methoxy-2-oxoethyl)phenyl]aminocarbonyl amino}-α,D-xylofuranose 1,2-O-isopropylidene-3-O-hexyl-5-deoxy-5-N-{[4-(2-methoxy-2-oxoethyl)phenyl]aminocarbonyl amino}-α,D-xylofuranose 1,2-O-isopropylidene-3-O-butyl-5-deoxy-5-N-{[4-(2-methoxy-2-oxoethyl)phenyl]aminocarbonyl amino}-α,D-xylofuranose 1,2-O-isopropylidene-3-O-methyl-5-deoxy-5-N-{[4-(2-methoxy-2-oxoethylphenyl]aminocarbonyl amino}-α,D-xylofuranose.

EXAMPLE 11

Preparation of 1,2-O-isopropylidene-3-O-dodecyl-5-deoxy-5-N-{[4-(2-hydroxy-2-oxoethyl)phenyl]aminocarbonylamino}-α,D-xylofuranose A mixture of ester as obtained in Example 10, Step 4 (2.7 gm) and aqueous NaOH (1N, 30 ml) was heated at 50° C. for 2 hours. The reaction was cooled in an ice-batch and acidified to pH 3 with 3N HCl, at which time a white solid separated, becoming an oil upon standing at room temperature. This product was extracted with ethyl acetate, washed with water, dried over anhydrous Na$_2$SO$_4$, and the solvent was removed under vacuum to obtain an oil. The crude product was purified by flash column chromatography by eluting with an ethyl acetate-hexane mixture (35:65) to obtain a white solid in 87% yield, m. p. 94–95° C.

The following compounds were prepared similarly:

1,2-O-isopropylidene-3-O-decyl-5-deoxy-5-N-{[4-(2-hydroxy-2-oxoethyl)phenyl]aminocarbonylamino}-α,D-xylofuranose 1,2-O-isopropylidene-3-O-hexyl-5-deoxy-5-N-{[4-(2-hydroxy-2-oxoethyl)phenyl]aminocarbonylamino}-α,D-xylofuranose 1,2-O-isopropylidene-3-O-butyl-5-deoxy-5-N-{[4-(2-hydroxy-2-oxoethyl)phenyl]aminocarbonylamino}-α,D-xylofuranose 1,2-O-isopropylidene-3-O-methyl-5-deoxy-5-N-{[4-(2-hydroxy-2-oxoethyl)phenyl]aminocarbonylamino}-α,D-xylofuranose.

EXAMPLE 12

Preparation of 1,2-O-isopropylidene-3-O-alkyl or alkylaryl-5-deoxy-5-N-{[4-(chloro,methyl or methoxy)-phenyl]aminocarbonylamino}-α,D-xylofuranose The desired amine, prepared similarly to the compound described in Example 10, Step 3, was reacted with an appropriate isocyanate, using the same procedure described in Example 10, Step 4, to obtain the desired compound.

The following compounds were prepared similarly:

1,2-O-isopropylidene-3-O-dodecyl-5-deoxy-5-N-{[4-chlorophenylaminocarbonylamino}-α,D-xylofuranose 1,2-O-isopropylidene-3-O-decyl-5-deoxy-5-N-{[4-chlorophenyl]aminocarbonylamino}α,D-xylofuranose 1,2-O-isopropylidene-3-O-hexyl-5-deoxy-5-N-{[4-chlorophenyl]aminocarbonylamino}α,D-xylofuranose 1,2-O-isopropylidene-3-O-butyl-5-deoxy-5-N-{[4-chlorophenyl]aminocarbonylamino}-α,D-xylofuranose 1,2-O-isopropylidene-3-O-methyl-5-deoxy-5-N-{[4-chlorophenyl]aminocarbonylamino}-α,D-xylofuranose 1,2-O-isopropylidene-3-O-dodecyl-5-deoxy-5-N-{[4-methoxyphenyl]aminocarbonylamino}α,D-xylofuranose 1,2-O-isopropylidene-3-O-decyl-5-deoxy-5-N-{[4-methoxyphenyl]aminocarbonylamino}α,D-xylofuranose 1,2-O-isopropylidene-3-O-hexyl-5-deoxy-5-N-{[4-methoxyphenyl]aminocarbonylamino}α,D-xylofuranose 1,2-O-isopropylidene-3-O-butyl-5-deoxy-5-N-{[4-methoxyphenyl]aminocarbonylamino}α,D-xylofuranose 1,2-O-isopropylidene-3-O-methyl-5-deoxy-5-N-{[4-methoxyphenyl]aminocarbonylamino}α,D-xylofuranose 1,2-O-isopropylidene-3-O-dodecyl-5-deoxy-5-N-{[4-tolyl]aminocarbonylamino}α,D-xylofuranose 1,2-O-isopropylidene-3-O-decyl-5-deoxy-5-N-{[4-tolyl]aminocarbonylamino}α,D-xylofuranose 1,2-O-isopropylidene-3-O-hexyl-5-deoxy-5-N-{[4-tolyl]aminocarbonylamino}α,D-xylofuranose 1,2-O-isopropylidene-3-O-butyl-5-deoxy-5-N-{[4-tolyl]aminocarbonylamino}α,D-xylofuranose 1,2-O-isopropylidene-3-O-methyl-5-deoxy-5-N-{[4-tolyl]aminocarbonylamino}α,D-xylofuranose.

EXAMPLE 13

Preparation of 1,2-O-isopropylidene-3-O-dodecyl-5-deoxy-5-N-{[aminocarbonyl amino]phenyl acetyl-L-Leucyl-α,L-Aspartyl-L-Valyl-L-Proline}-α,D-xylofuranose To a suspension of 1-(3-Dimethylaminopropyl)-3-ethylcarbodimide (EDC) (1.6 gm) and 1-hydroxybenzotriazole hydrate (HOBT) (1.1 gm) in DMF (60 ml) was added triethyl amine (1 ml) at room temperature and the reaction mixture was stirred for 30 minutes. Afterward, acid, as obtained in Example 11 (3.5 gm), and Leu-Asp(obz)Val-Pro(obzl) hydrochloride (4.09 gm) were added simultaneously to the reaction mixture and stirred for 24 hours. The reaction mixture was poured in water and extracted with CH$_2$Cl$_2$ (2 times 50 ml), followed by washing with saturated NaHCO$_3$ solution, water, brine and dried over anhydrous Na$_2$SO$_4$. The solvent was then removed at reduced pressure to get a white foamy solid, which was used for the next step without any purification.

To a solution of the above benzyl ester (0.8 gm) in ethyl acetate (70 ml) was added Pd/C (0.2 gm) at room temperature and subjected to hydrogenation using Parr shaker for 5 hours. The catalyst was filtered and ethyl acetate was removed to obtain a white solid in 56% yield.

The following compounds were prepared similarly:

1,2-O-isopropylidene-3-O-dodecyl-5-deoxy-5-N-{[aminocarbonylamino]phenylacetyl-α,L-Aspartyl-L-Valyl-L-Proline}-α,D-xylofuranose 1,2-O-isopropylidene-3-O-dodecyl-5-deoxy-5-N-{[aminocarbonylamino]phenylacetyl-L-Valyl-L-Proline}-α,D-xylofuranose.

EXAMPLE 14

Preparation of 1,2-O-isopropylidene-3-O-dodecyl-5-deoxy-5-N-{[4-(2-methoxy-2-oxoethyl)phenyl]aminocarbonylamino}-α,D-ribofuranose Step 1: 1,2-O-isopropylidene-3-O-dodecyl-4-carboxaldehyde-α,D-allofuranose 1,2-O-isopropylidene-3-O-dodecyl-α-D-allofuranose (prepared by the method reported in U.S. Pat. No. 4,996,195), was oxidized with $NaIO_4$, using the procedure described in Example 10, Step 1, to obtain a 76% yield. The following compounds were prepared similarly:

1,2-O-isopropylidene-3-O-methyl-4-carboxaldehyde-α,D-allofuranose
1,2-O-isopropylidene-3-O-butyl-4-carboxaldehyde-α,D-allofuranose
1,2-O-isopropylidene-3-O-hexyl-4-carboxaldehyde-α,D-allofuranose
1,2-O-isopropylidene-3-O-decyl-4-carboxaldehyde-α,D-allofuranose.

Step 2: 1,2-O-isopropylidene-3-O-dodecyl-4-oximino-α,D-allofuranose 1,2-O-isopropylidene-3-O-methyl-4-carboxaldehyde-α,D-allofuranose (obtained in Step 1) was reacted with hydroxyl amine hydrochloride, using the procedure described in Example 10, Step 2, to obtain an 80% yield.

The following compounds were prepared similarly:

1,2-O-isopropylidene-3-O-methyl-4-oximino-α,D-allofuranose
1,2-O-isopropylidene-3-O-butyl-4-oximino-α,D-allofuranose
1,2-O-isopropylidene-3-O-hexyl-4-oximino-α,D-allofuranose
1,2-O-isopropylidene-3-O-decyl-4-oximino-α,D-allofuranose.

Step 3: 1,2-O-isopropylidene-3-O-dodecyl-5-deoxy-5-amino-α,D-ribofuranose

Oxime, obtained in Step 2, was reduced with LAH, using the procedure outlined in Example 10, Step 3, to obtain a 79% yield.

The following compounds were prepared similarly:

1,2-O-isopropylidene-3-O-methyl-5-deoxy-5-amino-α,D-ribofuranose
1,2-O-isopropylidene-3-O-butyl-5-deoxy-5-amino-α,D-ribofuranose
1,2-O-isopropylidene-3-O-hexyl-5-deoxy-5-amino-α,D-ribofuranose
1,2-O-isopropylidene-3-O-decyl-5-deoxy-5-amino-α,D-ribofuranose.

Step 4: 1,2-O-isopropylidene-3-O-dodecyl-5-deoxy-5-N-{[4-(2-methoxy-2-oxoethyl) phenyl]aminocarbonylamino}-α,D-ribofuranose The amine obtained in Step 4 was reacted with methyl ester of p-isocyanate-4-phenyl acetic acid, using the method described in Example 10, Step 4, to obtain the desired ureido compound in 68% yield.

The following compounds were prepared similarly to those described in Example 14, Step 4:

1,2-O-isopropylidene-3-O-decyl-5-deoxy-5-N-{[4-(2-methoxy-2-oxoethyl)phenyl]aminocarbonylamino}-α,D-ribofuranose
1,2-O-isopropylidene-3-O-hexyl-5-deoxy-5-N-{[4-(2-methoxy-2-oxoethyl)phenyl]aminocarbonylamino}-α,D-ribofuranose
1,2-O-Isopropylidene-3-O-butyl-5-deoxy-5-N-{[4-(2-methoxy-2-oxoethyl)phenyl]aminocarbonylamino}-α,D-robofuanose
1,2-O-Isopropylidene-3-O-methyl-5-deoxy-5-N-{[4-(2-methoxy-2-oxoethyl)phenyl]aminocarbonylamino}-α,D-ribofuranose.

EXAMPLE 15

Preparation of 1,2-O-isopropylidene-3-O-dodecyl-5-deoxy-5-N-{[4-(2-hydroxy-2-oxoethyl)phenyl]aminocarbonylamino}-α,D-ribofuranose The ester obtained in Example 14, Step 4 was hydrolyzed with aqueous NaOH (1N), using the procedure outlined in Example 11, to obtain the desired compound in 70% yield.

The following compounds were prepared similarly:

1,2-O-isopropylidene-3-O-decyl-5-deoxy-5-N-{[4-(2-hydroxy-2-oxoethyl)phenyl]aminocarbonylamino}-α,D-ribofuranose
1,2-O-isopropylidene-3-O-hexyl-5-deoxy-5-N-{[4-(2-hydroxy-2-oxoethyl)phenyl]aminocarbonylamino}-α,D-ribofuranose
1,2-O-isopropylidene-3-O-butyl-5-deoxy-5-N-{[4-(2-hydroxy-2-oxoethyl)phenyl]aminocarbonylamino}-α,D-ribofuranose
1,2-O-isopropylidene-3-O-methyl-5-deoxy-5-N-{[4-(2-hydroxy-2-oxoethyl)phenyl]aminocarbonylamino}-α,D-ribofuranose.

EXAMPLE 16

Preparation of 1,2-O-isopropylidene-3-O-alkyl or alkylaryl-5-deoxy-5-N-{[4- (chloro, methyl or methoxy)-phenyl]aminocarbonylamino}-α,D-ribofuranose The desired amine, prepared similarly to that as described in Example 10, Step 3, was reacted with appropriate isocyanate, using the same procedure as described in Example 10, Step 4, to obtain the desired compound.

The following compounds were prepared similarly:

1,2-O-isopropylidene-3-O-dodecyl-5-deoxy-5-N-{[4-chlorophenyl]aminocarbonylamino}α,D-ribofuranose
1,2-O-isopropylidene-3-O-decyl-5-deoxy-5-N-{[4-chlorophenyl]aminocarbonylamino}α,D-ribofuranose
1,2-O-isopropylidene-3-O-heptyl-5-deoxy-5-N-{[4-chlorophenyl]aminocarbonylamino}α,D-ribofuranose
1,2-O-isopropylidene-3-O-butyl-5-deoxy-5-N-{[4-chlorophenyl]aminocarbonylamino}α,D-ribofuranose
1,2-O-isopropylidene-3-O-methyl-5-deoxy-5-N-{[4-chlorophenyl]aminocarbonylamino}α,D-ribofuranose
b 1,2-O-isopropylidene-3-O-dodecyl-5-deoxy-5-N-{[4-methoxyphenyl]aminocarbonylamino}α,D-ribofuranose
1,2-O-isopropylidene-3-O-decyl-5-deoxy-5-N-{[4-methoxyphenyl]aminocarbonylamino}α,D-ribofuranose
1,2-O-isopropylidene-3-O-heptyl-5-deoxy-5-N-{[4-methoxyphenyl]aminocarbonylamino}α,D-ribofuranose
1,2-O-isopropylidene-3-O-butyl-5-deoxy-5-N-{[4-methoxyphenyl]aminocarbonylamino}α,D-ribofuranose 1,2-O-isopropylidene-3-O-methyl-5-deoxy-5-N-{[4-methoxyphenyl]aminocarbonylamino}α,D-ribofuranose
1,2-O-isopropylidene-3-O-dodecyl-5-deoxy-5-N-{[4-tolyl]aminocarbonylamino}α,D-ribofuranose
1,2-O-isopropylidene-3-O-decyl-5-deoxy-5-N-{[4-tolyl]aminocarbonylamino}α,D-ribofuranose
1,2-O-isopropylidene-3-O-heptyl-5-deoxy-5-N-{[4-tolyl]aminocarbonylamino}α,D-ribofuranose
1,2-O-isopropylidene-3-O-butyl-5-deoxy-5-N-{[4-tolyl]aminocarbonylamino}α,D-ribofuranose
1,2-O-isopropylidene-3-O-methyl-5-deoxy-5-N-{[4-tolyl]aminocarbonylamino}α,D-ribofuranose.

EXAMPLE 17

Preparation of 1,2-O-isopropylidene-3-O-dodecyl-5-deoxy-5-N-{[aminocarbonyl aminophenyl]acetyl-L-Leucyl-α,L-Aspartyl-L-Valyl-L-Proline}-α,D-ribofuranose.

The above compound was prepared by reacting the acid obtained in Example 15 with Leu-Asp(obzl) Val-Pro (obzl) hydrochloride, following the procedure described in Example 13, to obtain a 74% yield.

The following compounds were prepared similarly:

1,2-O-isopropylidene-3-O-dodecyl-5-deoxy-5-N-{[aminocarbonylaminophenyl]acetyl-α,L-Aspartyl-L-Valyl-L-Proline}-α,D-ribofuranose
1,2-O-isopropylidene-3-O-dodecyl-5-deoxy-5-N-{[aminocarbonylaminophenyl]acetyl-L-Valyl-L-Proline}-α,D-ribofuranose.

EXAMPLE 18

Preparation of 2,3-O-isopropylidene-1-O-dodecyl-5-deoxy-5-N-{[4-(2-methoxy-2-oxoethyl)phenyl]aminocarbonylamino}-α,D-lyxofuranoside Step 1: 2,3-O-isopropylidine-1-O-dodecyl-5-deoxy-5-azido α,D-lyxofuranoside A mixture of 2,3-O-isopropylidine-1-O-dodecyl-5-p-tosyl-α,D-lyxofuranoside (using the method reported in U.S. Pat. No. 5,367,062) (8 gm), NaN₃ (8 gm), and DMF (80 ml) was heated at 100° C. for 9 hours. The solvent was removed under vacuum and the obtained residue was dissolved in ethyl acetate and washed with water (2 times 50 ml). The organic layer was dried over anhydrous Na$_2$SO$_4$, filtered and evaporated to dryness under vacuum. The crude material was purified by flash column chromatography and eluted with a 2% ethyl acetate-hexane mixture to obtain an oil in 83% yield of the pure product.

The following compounds were prepared similarly:

2,3-O-isopropylidine-1-O-methyl-5 -deoxy-5 -azido-α,D-lyxofuranoside
2,3-O-isopropylidine-1-O-butyl-5-deoxy-5-azido-α,D-lyxofuranoside
2,3-O-isopropylidine-1-O-heptyl-5-deoxy-5-azido-α,D-lyxofuranoside
2,3-O-isopropylidine-1-O-decyl-5-deoxy-5-azido-α,D-lyxofuranoside.

Step 2: 2,3-O-isopropylidine-1-O-dodecyl-5-deoxy-5-amino-α,D-lyxofuranoside

To a solution of LAH (5 gm) in dry THF (100 ml) at 0–5° C. was added the solution of the above compound (3 gm in 10 ml THF) dropwise. Once the addition was complete, the reaction was stirred at room temperature for 2 hours. Excess LAH was decomposed by the addition of the ice-water mixture. The reaction mixture was then filtered through celite, washed with 100 ml of THF, and the solvent was removed under vacuum. The residue was dissolved in 200 ml of ethyl acetate and washed with water and brine. The solvent was dried over anhydrous Na$_2$SO$_4$ and removed under vacuum to obtain an oil in 65% yield.

The following compounds were prepared similarly:

2,3-O-isopropylidine-1-O-methyl-5-deoxy-5-amino-α,D-lyxofuranoside
2,3-O-isopropylidine-1-O-butyl-5-deoxy-5-amino-α,D-lyxofuranoside
2,3-O-isopropylidine-1-O-heptyl-5-deoxy-5-amino-α,D-lyxofuranoside
2,3-O-isopropylidine-1-O-decyl-5-deoxy-5-amino-α,D-lyxofuranoside.

Step 3: 2,3-O-isopropylidene-1-O-dodecyl-5-deoxy-5-N-{[4-(2-methoxy-2-oxo ethyl)phenyl]aminocarbonylamino}-α,D-lyxofuranoside To a cold (0–5° C.) solution of the above amine (0.5 gm, 1.4 mmol) in dry CH$_2$Cl$_2$ (10 ml) was added a solution of methyl ester of p-isocyanate-4-phenyl acetic acid (260 m gm, 1.4 mmol) in dry CH$_2$Cl$_2$ (5 ml). The reaction mixture was stirred at the same temperature for 3 hours, after which 90 ml more of CH$_2$Cl$_2$ were added to it, washed with water (2 times 10 ml) and brine (2 times 10 ml), dried over anhydrous Na$_2$SO$_4$, and the solvent was removed under vacuum to obtain an oil. The product was purified by flash column chromatography and eluted with an ethyl acetate hexane mixture (20:80) to obtain a white solid in 80% yield of the pure product.

The following compounds were prepared similarly to those described in Example 18, Step 3:

2,3-O-isopropylidene-1-O-methyl-5-deoxy-5-N-{[4-(2-methoxy-2-oxoethyl)phenyl]aminocarbonylamino}-α,D-lyxofuranoside
2,3-O-isopropylidene-1-O-butyl-5-deoxy-5-N-{[4-(2-methoxy-2-oxoethyl)phenyl]aminocarbonylamino}-α,D-lyxofuranoside
2,3-O-isopropylidene-1-O-heptyl-5-deoxy-5-N-{[4-(2-methoxy-2-oxoethyl)phenyl]aminocarbonylamino}-α,D-lyxofuranoside
2,3-O-isopropylidene-1-O-decyl-5-deoxy-5-N-{[4-(2-methoxy-2-oxoethyl)phenyl]aminocarbonylamino}-α,D-lyxofuranoside.

EXAMPLE 19

Preparation of 2,3-O-isopropylidene-1-O-dodecyl-5-deoxy-5-N-{[4-(2-hydroxy-2-oxo ethyl)phenyl]aminocarbonylamino}α,D-lyxofuranoside A mixture of ester as obtained in Example 18, Step 3 (0.3 gm) and aqueous NaOH (10 ml) (1N) was heated at 50 ° C. for 2 hours. The reaction was cooled in an ice-water mixture and acidified to pH 3 with 3N HCl, after which a white solid separated, becoming an oil upon standing at room temperature. The product was extracted with ethyl acetate and washed with water, dried over anhydrous Na$_2$SO$_4$ and the solvent removed under vacuum to obtain an oil. The crude product was purified by flash column chromatography by eluting with an ethyl acetate-hexane mixture (35:65) to obtain an oil in 71% yield.

The following compounds were prepared similarly:

2,3-O-isopropylidene-1-O-methyl-5-deoxy-5-N-{[4-(2-hydroxy-2-oxoethyl)phenyl]aminocarbonylamino}-α,D-lyxofuranoside
2,3-O-isopropylidene-1-O-butyl-5-deoxy-5-N-{[4-(2-hydroxy-2-oxoethyl)phenyl]aminocarbonylamino}-α,D-lyxofuranoside
2,3-O-isopropylidene-1-O-heptyl-5-deoxy-5-N-{[4-(2-hydroxy-2-oxoethyl)phenyl]aminocarbonylamino}-α,D-lyxofuranoside
2,3-O-isopropylidene-1-O-decyl-5-deoxy-5-N-{[4-(2-hydroxy-2-oxoethyl)phenyl]aminocarbonylamino}-α,D-lyxofuranoside

EXAMPLE 20

Preparation of 2,3-O-isopropylidene-1-O-alkyl or alkyl aryl-5-deoxy-5-N-{[4-(chloro, methyl or methoxy)-phenyl]aminocarbonylamino}-α,D-lyxofuranoside The desired amine, prepared similarly as described in Example 18, Step 2, was reacted with an appropriate isocyanate, using the procedure described in Example 18, Step 3, to obtain the desired compound.

The following compounds were prepared similarly:

2,3-O-isopropylidene-1-O-methyl-5-deoxy-5-N-{[4-chlorophenyl]aminocarbonylamino}α,D-lyxofuranoside
2,3-O-isopropylidene-1-O-butyl-5-deoxy-5-N-{[4-chlorophenyl]aminocarbonylamino}α,D-lyxofuranoside
2,3-O-isopropylidene-1O-heptyl-5-deoxy-5-N-{[4-chlorophenyl]aminocarbonylamino}α,D-lyxofuranoside
2,3-O-isopropylidene-1O-decyl-5-deoxy-5-N-{[4-chlorophenyl]aminocarbonylamino}α,D-lyxofuranoside
b 2,3-O-isopropylidene-1-O-dodecyl-5-deoxy-5-N-{[4-chlorophenyl]aminocarbonylamino}α,D-lyxofuranoside
2,3-O-isopropylidene-1-O-methyl-5-deoxy-5-N-{[4-methoxyphenyl]aminocarbonylamino}α,D-lyxofuranoside
2,3-O-isopropylidene-1-O-butyl-5-deoxy-5-N-{[4-methoxyphenyl]aminocarbonylamino}α,D-lyxofuranoside
2,3-O-isopropylidene-1-O-heptyl-5-deoxy-5-N-{[4-methoxyphenyl]aminocarbonylamino}α,D-lyxofuranoside
2,3-O-isopropylidene-1-O-decyl-5 -deoxy-5-N-{[4-methoxyphenyl]aminocarbonylamino}α,D-lyxofuranoside
2,3-O-isopropylidene-1-O-dodecyl-5 -deoxy-5-N-{[4-methox yphenyl]aminocarbonylamino}α,D-lyxofuranoside
2,3-O-isopropylidene-1-O-methyl-5-deoxy-5-N-{[4-tolyl] aminocarbonylamino}α,D-lyxofuranoside
2,3-O-isopropylidene-1-O-butyl-5-deoxy-5-N-{[4-tolyl] aminocarbonylamino}α,D-lyxofuranoside
2,3-O-isopropylidene-1-O-heptyl-5-deoxy-5-N-{[4-tolyl] aminocarbonylamino}α,D-lyxofuranoside
2,3-O-isopropylidene-1-O-decyl-5-deoxy-5-N-{[4-tolyl] aminocarbonylamino}α,D-lyxofuranoside
2,3-O-isopropylidene-1-O-dodecyl-5-deoxy-5-N-{[4-tolyl] aminocarbonylamino}α,D-lyxofuranoside.

EXAMPLE 21

Preparation of 2,3-O-isopropylidene-1-O-dodecyl-5-deoxy-5-N-{[aminocarbonyl amino]phenylacetyl-L-Leucyl-α,L-Aspartyl-L-Valyl-L-Proline}-α,D-lyxofuranoside To a suspension of EDC (2.30 gm) and HOBT (1.53 gm) in ethyl acetate (100 ml) was added triethyl amine (1 ml) at room temperature. The reaction mixture was stirred for 30 minutes, after which the acid (as obtained in Example 19) (5.3 gm) and Leu-Asp(obzl)Val-Pro(obzl) hydrochloride (6.58 gm) were added simultaneously to the reaction mixture and stirred for 24 hours. The reaction mixture was poured in water and extracted with $CH_2Cl_2$ (2 times 50 ml), followed by washing with saturated $NaHCO_3$ solution, water and brine, and dried over anhydrous $Na_2SO_4$, and the solvent was removed at reduced pressure to obtain a white foamy solid, which was used for the next step without any purification.

To a solution of the above, benzyl ester (2 gm) in ethyl acetate (50 ml) was added Pd/C (10% w/w, 0.2 gm) at room temperature and subjected to hydrogenation using Parr shaker for 5 hours. The catalyst was filtered and ethyl acetate was removed to obtain a low melting solid in 84% yield. A product shows a single homogeneous spot on TLC.

The following compounds were prepared similarly:

2,3-O-isopropylidene-1-O-dodecyl-5-deoxy-5-N-{ [aminocarbonylamino]phenylacetyl-α,L-Aspartyl-L-Valyl-L-Proline}-α,D-lyxofuranoside
2,3-O-isopropylidene-1-O-dodecyl-5-deoxy-5-N-{ [aminocarbonylamino]phenylacetyl-L-Valyl-L-Proline}-α,D-lyxofuranoside.

EXAMPLE 22

Preparation of 2,3-O-isopropylidene-1-carbonyl-L-Leucyl-α,L-Aspartyl-L-Valyl-LProline-α, L-xylo-2-hexulofuranosonic acid Step 1: 2,3;4,6-Di-O-isopropylidene-1-carbonyl-L-Leucyl-α,L-Aspartyl-L-Valyl-L-Pro-line-α,L-xylo-2-hexulofuranosonic acid To a suspension of EDC (1.15 gm), HOBT (0.76 gm) in DMF (10 ml) was added triethyl amine (1.5 gm) at room temperature and the reaction mixture was stirred for 30 minutes. Afterward, acid (1.46 gm) and Leu-Asp(obzl)Val-Pro(obzl) hydrochloride were added simultaneously to the reaction mixture and stirred for 24 hours. The reaction mixture was poured in water and extracted with $CH_2Cl_2$. (2 times 50 ml), followed by washing with saturated $NaHCO_3$, water, brine and dried over anhydrous $Na_2SO_4$, and solvent was removed at reduced pressure to obtain a white foamy solid (3.6 gm), which was used for the next step without any purification.

To a solution of the above, together with benzyl ester (3.6 gm) in ethyl acetate (70 ml) was added Pd/C (2.0 gm) at room temperature and subjected to hydrogenation using Parr shaker for 5 hours. The catalyst was filtered and ethyl acetate was removed to obtain a white solid in 91% yield. The product was recrystallized from ethyl acetate-hexane mixture.

The following compounds were prepared similarly:

2,3;4,6-Di-O-isopropylidene-1-carbonyl-α, L-Aspartyl-L-Valyl-L-Proline-α,L-xylo-2-hexulofuranosonic acid
2,3;4,6-Di-O-isopropylidene-1 -carbonyl-L-Valyl-L-Proline-α,L-xylo-2-hexulofuranosonic acid.

Step 2: 2,3-O-isopropylidene-carbonyl-L-Leucyl-α, L-Aspartyl-L-Valyl-L-Proline-α, L-xylo-2-hexulofuranosonic acid To a solution of the compound (0.5 gm) obtained in Step 1 in THF (10 ml) was added a 30% solution of perchloric acid (0.5 ml) dropwise at 0–5° C. and the reaction mixture was stirred at this temperature for 4 hours. The reaction was quenched with a saturated solution of potassium carbonate and the solid salt that was formed was filtered and washed with 20 ml of THF. The solvent from the filtrate was evaporated under vacuum completely, the residue was dissolved in ethyl acetate washed with water and brine. The organic layer was dried over anhydrous $Na_2SO_4$ and the solvent was removed to obtain a low melting solid in 90% yield.

The following compounds were prepared similarly:

2,3-O-isopropylidene-carbonyl-α,L-Aspartyl-L-Valyl-L-Proline-α,L-xylo-2-hexulofuranosonic acid
2,3-O-isopropylidene-carbonyl-L-Valyl-L-Proline-α,L-xylo-2-hexulofuranosonic acid.

EXAMPLE 23

Preparation of 2,3-O-Isopropylidene-1-deoxy-1-N-{[4-(2-methoxy-2oxoethyl), phenyl aminocarbonylamino}α,L-xylo-2-hexulofuranose Step 1: 2,3;4,6-Di-O-isopropylidene-1-p-tosyl-α,L-xylo-2-hexulofuranose To a solution of 2,3;4,6-Di-O-isopropylidene-α,D-xylo-2-hexulofuranose (prepared by the method reported in U.S. Pat. No. 5,637,570) (8.0 gm, 30.65 mmol) in dry pyridine (50 ml) was added p-tolune sulphonyl chloride (p-Tscl) (6.4 gm, 33.71 m mole) portionwise at 0–5° C. Thereafter, the reaction mixture was stirred at room temperature for 12 hours, pyridine was removed under vacuum, water was added to it, and extracted with ethyl acetate. The ethyl acetate layer was washed with saturated $NaHCO_3$ solution and brine, dried over anhydrous $Na_2SO_4$. The solvent was removed under vacuum to obtain an oil, which was purified by column chromatography using 5% ethyl acetate in hexane to obtain a 64% yield of the pure product.

Step 2: 2,3;4,6-Di-O-isopropylidene-1-deoxy-1-azido-α,L-xylo-2-hexulofuranose

A mixture of tosylate (9.0 gm), $NaN_3$ (9.0 gm) and DMF (100 ml) was heated at 100° C. for 12 hours. DMF removed under vacuum, water was added to it, and extracted with ethyl acetate. The combined extract was washed with water, brine, then dried over anhydrous $Na_2SO_4$, after which the solvent was removed under vacuum to obtain an oil. The crude product was purified by column chromatography using 5% ethyl acetate in hexane. The yield of the pure product was 84%.

Step 3: 2,3;4,6-Di-O-isopropylidene-1-deoxy-1-amino-α,L-xylo-2-hexulofuranose

To a solution of $NaN_3$ (4.0 gm) in THF (50 ml) was added LAH (3.0 gm) portionwise at 0–5° C. and stirred at this temperature for 4 hours. Excess LAH was removed by decomposition with ice-water, the separated solid was filtered and washed with THF. The solvent was removed under vacuum, ethyl acetate was added to it, washed with water and brine, and dried over anhydrous $Na_2SO_4$. The solvent was then removed under vacuum to obtain an oil was purified by column chromatography using 10% ethyl acetate in hexane. The yield of the pure product was 86%.

Step 4: 2,3;4,6-Di-O-isopropylidene-1-deoxy-1-N-{[4-(2-methoxy-2oxoethyl))phenyl aminocarbonylamino}-α,L-xylo-2-hexulofuranose To a solution of amine (0.5 gm, 1.92 mmol) in dry $CH_2Cl_2$ (10 ml) was added a solution of methyl ester of p-isocyanate-4-phenyl acetic acid (1.92 mmol) in 5 ml of dry $CH_2Cl_2$ at 0–5° C. The reaction was stirred at this temperature for 2 hours. The $CH_2Cl_2$ layer was washed with water, dried over anhydrous $Na_2SO_4$, and the solvent was removed under vacuum to obtain an oil, which was purified by column chromatography (100–200 mesh) by eluting hexane in 30% ethyl acetate in 64% yield.

The following compounds were prepared similarly:

2,3;4,6-Di-O-isopropylidene-1-deoxy-1-N-{[4-chlorophenyl]aminocarbonylamino}-α,L-xylo-2-hexulofuranose
2,3;4,6-Di-O-isopropylidene-1-deoxy-1-N-{[4-methoxyphenyl]aminocarbonylamino}-α,L-xylo-2-hexulofuranose
2,3;4,6-Di-O-isopropylidene-1-deoxy-1-N-{[4-tolyl]aminocarbonylamino}-α,L-xylo-2-hexulofuranose.

Step 5: 2,3-O-Isopropylidene-1-deoxy-1-N-{[4-(2-methoxy-2oxoethyl))phenylamino car-bonylamino}-α,L-xylo-2-hexulofuranose To a solution of the compound (0.5 gm) obtained in Step 5 in THF (10 ml) was added a 30% solution of perchloric acid (0.5 ml) dropwise at 0–5° C. The reaction was stirred at this temperature for 4 hours. The reaction was quenched with a saturated solution of potassium carbonate, and the formed solid salt was filtered and washed with 20 ml THF. The solvent was evaporated under vacuum, the residue dissolved in ethyl acetate, washed with water and brine, and the organic layer was dried over anhydrous $Na_2SO_4$ and removed under vacuum to obtain an oil in 52% yield after purification by column chromatography and eluting with 10% ethyl acetate in hexane.

The following compounds were prepared similarly:

2,3-O-isopropylidene-1-deoxy-1-N-{[4-chlorophenyl]aminocarbonylamino}-α,L-xylo-2-hexulofuranose
2,3-O-isopropylidene-1-deoxy-1-N-{[4-methoxyphenyl]aminocarbonylamino}-α,L-xylo-2-hexulofuranose
2,3-O-isopropylidene-1-deoxy-1-N-{[4-tolyl]aminocarbonylamino}-α,L-xylo-2-hexulofuranose.

EXAMPLE 24

Preparation of 2,3-O-isopropylidene-1-deoxy-1-N-{[4-(2-hydroxy-2oxoethyl))phenyl aminocarbonylamino}α,L-xylo-2-hexulofuranose A mixture of ester, as obtained in Example 23, Step 5 (0.5 g) and aqueous NaOH (10 ml, 1N) was heated at 50° C. for two hours. The reaction was cooled in an ice-batch and acidified to pH 3 with 3N HCl, at which time a white solid separated, which became oil upon standing at room temperature. The product was extracted with ethyl acetate and washed with water, dried over anhydrous $Na_2SO_4$, and the solvent was removed under vacuum to obtain an oil. The crude product was purified by flash column chromatography by eluting with a ethyl acetate-hexane mixture (35:65) to obtain an oil in 89% yield.

EXAMPLE 25

Preparation of 2,3-O-isopropylidene-1deoxy-1-N-{[aminocarbonylaminophenyl acetyl-L-Leucyl-α,L-Aspartyl-L-Valyl-L-Proline)}-α,L-xylo-2-hexulofuranose To a suspension of EDC (0.23 gm), HOBT (0.153 gm) in DMF (60 ml) was added triethyl amine (0.30 gm) at room temperature and the reaction mixture was stirred for 30 minutes. Then the acid, as obtained in Example 24 (0.43 gm), and Leu-Asp(obzl)Val-Pro(obzl) hydrochloride (0.65 gm) were added simultaneously to the above reaction mixture and stirred for 24 hours. The reaction mixture was poured in water and extracted with $CH_2Cl_2$ (2 times 50 ml), followed by washing with saturated $NaHCO_3$ solution, water and brine, and dried over anhydrous $Na_2SO_4$. The solvent was removed at reduced pressure to obtain a white foamy solid (0.72 gm), which was used for the next step without any purification.

To a solution of the above, benzyl ester (0.7 gm) in ethyl acetate (15 ml) was added Pd/C (10% w/w) (0.1 gm) at room temperature and subjected to hydrogenation using Parr shaker for 5 hours. The catalyst was filtered and the ethyl acetate was removed to obtain a white solid. The crude product was recrystallized with an ethyl acetate-hexane mixture to obtain a pure product yield of 82%.

The following compounds were prepared similarly:

2,3-O-isopropylidene-1deoxy-1-N-{[aminocarbonylaminophenylacetyl-α,L-Aspartyl-L-Valyl-L-Proline)}-α,L-xylo-2-hexulofuranose
2,3-O-isopropylidene-1deoxy-1-N-{[aminocarbonylaminophenylacetyl-L-Valyl-L-Proline)}-α,L-xylo-2-hexulofuranose.

Pharmacological Activity

The compounds of the present invention have demonstrated inhibitory activity in cell adhesion assay and anti-inflammatory effects in biological assay. Standard assays have been performed on most of the compounds of the present invention to ascertain the adhesion inhibitory and anti-inflammatory activity. These assays include:

1) in vitro cell adhesion assay
2) mouse Ear Swelling Test (MEST)

The in vitro cell adhesion assay was used to measure the effect of a test compound on adhesion of human T cell line (Jurkat J6) on surfaces coated with VCAM-1. The MEST assesses the ability of the experimental compounds to inhibit the delayed-type hypersensitivity response of sensitized mice against a potent allergen, 1,4-Dinitrofluoro benzene. These two assays are appropriate for screening compounds for two different activities. The cell adhesion assay determines the effect of compounds on the interaction of $VLA_4$ molecules expressed on the surface of Jurkat cells with its counter-receptor, VCAM-1, immobilized on microtitre plate surface. Conversely, the MEST determines the potency of compounds to inhibit the murine contact hypersensitivity response induced by exposing mice to the potent allergen 1,4-Dinitrofluoro benzene. The Chisolm et al method was used in this respect (Chisolm et al, Eur. J. Immunology 1993;23:682).

Inhibition of $VLA_4$-dependent Adhesion to VCAM-1

This assay was used to assess the ability of the compounds of the present invention to inhibit the $VLA_4$-VCAM-1 interaction utilizing recombinant human VCAM-1. The adhesion of $VLA_4$-positive Jurkat cells to recombinant VCAM-1 in the presence of the compound is quantitated using the MTT [3-(4,5-dimethylthiazol-2-yl)-2,5-diphenyltetrazolium bromide] dye reduction method. Briefly, the following protocol was used:

1. Preparation of VCAM-1-coated Microtitre Pates

Polystyrene 96 well Maxisorp microtitre plates (Nunc, USA) were coated with 0.5 µg/ml recombinant human VCAM-1 (R&D Systems Inc, USA) dissolved in 0.05 M $NaHCO_3$ (15 mM $NaHCO_3$ and 35 mM $Na_2CO_3$; pH 9.2). Some wells were not coated with VCAM-1 in order to assess non-specific cell binding. The plate was then incubated overnight at 4° C.

Following this incubation, the contents of the wells were removed by inverting and blotting the plate. All wells were washed twice with phosphate buffered saline (PBS) and then blocked with 300 µL of 3% bovine serum albumin (BSA) in PBS for a minimum of 1 hr at 37° C.

Preparation of Jurkat Cells

The J6 clone of the Jurkat cell line was procured from the National Center for Cell Sciences, Pune, India and maintained in RPMI 1640 culture medium containing 5% fetal calf serum. Prior to running the assay, exponentially growing cells were harvested by centrifugation at 200 g for 10 minutes in Beckman GS15 centrifuge. The cells were washed and suspended in serum-free culture medium. The cell count was adjusted to 2 times $10^6$ cells/ml.

3. Running the Assay

Compounds were dissolved in dimethyl sulfoxide (DMSO) and diluted further in PBS at 2 times the final concentration to be used in the assay. All compounds were tested at concentrations ranging from 10 ng/ml to 1 mg/ml. Immediately prior to running the assay, the BSA blocking solution was removed from the 96 well plates and each well was washed twice with PBS. Equal volumes (50 µL each) of compound and cell suspension ($2 \times 10^6$ cells/ml) were added onto VCAM-1-coated wells and incubated at 37° C. on a plate shaker for 15 minutes. The plates were then transferred to a $CO_2$ incubator and incubated further for 1 hour at 37° C.

At the end of 1 hour, the plates were gently flicked to remove non-adhered cells and washed once gently with PBS.

4. Cell Quantitation

The adhered cells were quantitated using the MTT dye reduction method (MTT-Sigma). For this purpose, 250 µL of freshly prepared MTT solution in RPMI 1640 culture medium without fetal calf serum (0.2 mg/ml) was added to all wells and incubated at 37° C. in the $CO_2$ incubator for 4 hours.

At the end of 4 hours, the supernatant medium was aspirated gently and blue crystals were dissolved in 100 µL DMSO (Sigma). The plates were read at 570 nm using the Dynatech ELISA reader.

5. Calculations of Percent Adsorption and $IC_{50}$ Values

The percent adsorption was calculated using the following formula:

$$\% \text{ Adsorption} = \frac{\text{Mean } OD \text{ of test wells} - \text{Mean } OD \text{ of blank wells}}{\text{Mean } OD \text{ of cell control wells} - \text{Mean } OD \text{ of blank wells}} \times 100$$

The percent adsorption values were then plotted against the log (concentration) of compounds in Graph Pad Prizm software (Graph Pad Software, USA) and analyzed by Sigmoid Dose Response curve fit, and the $IC_{50}$ value was determined. The results of the cell adhesion assay are listed in Table 1.

TABLE 1

Results of in vitro cell adhesion assay

| St. No. | COMPOUND NO. | $IC_{50}$ |
|---|---|---|
| 1 | 33 | >1000 |
| 2 | 38 | 223.9 |
| 3 | 43 | 120.2 |
| 4 | 53 | 7.49 |
| 5 | 73 | 114.15 |
| 6 | 74 | 116.3 |
| 7 | 75 | 38.9 |
| 8 | 76 | 3.69 |
| 9 | 79 | 53.7 |
| 10 | 81 | 181.57 |
| 11 | 86 | 134.9 |
| 12 | 91 | 275.4 |
| 13 | 96 | 72.55 |
| 14 | 97 | 156.85 |
| 15 | 98 | 140.95 |
| 16 | 99 | >100 |
| 17 | 100 | >1000 |
| 18 | 104 | >100 |
| 19 | 110 | >100 |
| 20 | 122* | 8.45 |
| 21 | 122** | 4.18 |
| 22 | 123 | 120.23 |

*Ditris salt, **Disodium salt

Mouse Ear Swelling Test

We tested the efficacy of compounds synthesized in this invention to inhibit the act hypersensitivity in Swiss mice as follows:

1. Sensitization of Mice 20 to 25 gm female Swiss albino mice (animals procured from National Institute of Immunology, New Delhi, India and maintained in our Experimental Animal Facility) were anesthetized with anesthetic ether (Sisco Research Laboratories Ltd., India). A 2 cm² patch of dorsal skin was shaved using a hair clipper. The exposed skin was then dermabraded using No. 100 sandpaper gently. 25 µL freshly prepared 0.5% 1,4-Dinitrofluoro benzene in 4:1 (v/v) acetone:olive oil solution was then topically applied onto the dermabraded skin to encourage a mild inflammation reaction. Twenty-four hours after the initial sensitization, the mice were again sensitized with 25 µL freshly prepared 0.5% 1,4-Dinitrofluor benzene (DNFB) in 4:1 (v/v) acetone:olive oil solution on the same dermabraded site as before. The second sensitization was performed while restraining the non-anesthetized, conscious mouse.

2. Administration of Compound

On day 5, compounds were dissolved in an aqueous solvent (pyrogen-free water, alkaline water, or ethanol) and further diluted in pyrogen-free water to prepare appropriate doses. Solutions were administered by intravenous, subcutaneous or oral route.

3. Challenge and Measurement of Ear Thickness

Two hours following administration of the compounds, the animals were physically restrained and painted with 25 µL of freshly prepared 0.5% DNFB in 4:1 (v/v) acetone:olive oil solution on the right ear. The thickness of the right ear was measured using a Series 300 Odimeter (Dyer Gauge Inc, USA) at the time of challenge (0 hr), 4 hours and 24 hours after challenge while physically restraining the non-anesthetized mice. In a separate experiment, it was ascertained that 4:1 (v/v) acetone:olive oil vehicle has no effect on ear thickness.

4. Determination of Effective Concentration of the Compounds

Inhibition of the ear swelling was judged by comparison of treated groups with their negative control groups. Percent inhibition was calculated as:

$$\% \text{ Swelling} = \frac{S_{TEST} - S_{TEST-zero}}{S_{NC} - S_{NCzero}} \times 100$$

where $S_{TEST}$=Mean ear thickness in test group at 24 hours after challenge $S_{TEST-zero}$=Mean ear thickness in test group at zero hours after challenge $S_{NC}$=Mean ear thickness in negative control group at 24 hours after challenge $S_{NC-zero}$=Mean ear thickness in negative control group at zero hours after challenge The percentage inhibition of swelling obtained by the above calculation was plotted against log dose using the Graph Pad Prizm software and, from this plot, the log dose corresponding to 30% inhibition (log $ED_{30}$) and 40% (log $ED_{40}$) inhibition was determined. The $ED_{30}$ and $ED_{40}$ values for some of the compounds are listed in Table 2.

TABLE 2

Results of Mouse Ear Swelling Test

| No | COMPOUND NO. | Route | $EC_{30}$ | $EC_{40}$ |
|---|---|---|---|---|
| 1 | 53 | I.V. | 10 µg | 70 µg |
|  |  | S.C. | 500 ng | 10 µg |
|  |  | Oral | 1 µg/kg | — |
| 2 | 76 | Oral | 0.29 µg/kg | 81.28 µg/kg |
| 3 | 122* | I.V. | 12 mg | — |
| 4 | 122** | I.V. | 8 mg | — |

*Ditris salt, **Disodium salt

Aqueous solutions of appropriate doses (1 µg/kg to 100 mg/kg) were administered by intravenous route 2 hrs before challenge and their effect on ear thickness was measured. Concentrations inhibiting ear swelling by 30% and 40% were determined and expressed as amount (ng, µg or mg) per Kg body weight.

While the present invention has been described in terms of its specific embodiments, certain modifications and equivalents will be apparent to those skilled in the art and are intended to be included within the scope of the present invention, which is to be limited only by scope of the appended claims.

What is claimed is:

1. A compound having the structure of Formula I:

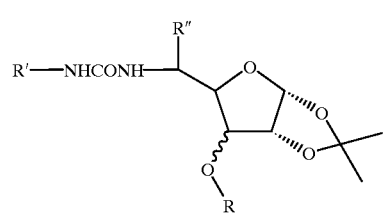

Formula I and its pharmaceutically acceptable salts, esters, enantiomers, diastereomers, N-oxides, amides, or prodrugs, wherein R is $C_1$ to $C_{15}$ alkyl, alkene, straight chain or branched alkyne, aryl, substituted aryl or alkylaryl, R' is $SO_2C_6H_5$, $SO_2C_6H_4CH_3$-p, or $SO_2C_6H_4Cl$-p, phenyl, or $C_6H_4$—R'''-p wherein R''' is being Cl, $NO_2$, $OCH_3$, $CH_3$, $CH_2COOH$, $CH_2COOCH_3$, $CH_2COLDVP$, $CH_2CODVP$, $CH_2COVP$, wherein LDVP, DVP and VP represent tripeptide (Leucyl-aspartyl-valyl-prolyl), tripeptide (aspartyl-valyl-prolyl) and (valyl-prolyl), respectively, R'' is H or $CH_3$, and (∿∿) represents epiglucofuranose, epiallofuranose, xylofuranose or ribofuranose configurations.

2. A compound having the structure of Formula II comprising epimannofuranoside or lyxofuranoside derivatives

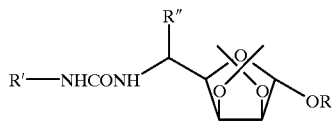

Formula II and its pharmaceutically acceptable salts, esters, enantiomers, diastereomers, N-oxides, amides, or prodrugs, wherein R is $C_1$ to $C_{15}$ alkyl, alkene, straight chain or branched alkyne, aryl, substituted aryl or alkylaryl, R' is $SO_2C_6H_5$, $SO_2C_6H_4CH_3$-p, or $SO_2C_6H_4Cl$-p, phenyl, or $C_6H_4$—R'''-p wherein R''' is being Cl, $NO_2$, $OCH_3$, $CH_3$, $CH_2COOH$, $CH_2COOCH_3$, $CH_2COLDVP$, $CH_2CODVP$, $CH_2COVP$, wherein LDVP, DVP and VP represent tripeptide (Leucyl-aspartyl-valyl-prolyl), tripeptide (aspartyl-valyl-prolyl) and (valyl-prolyl), respectively, and R'' is H or $CH_3$.

3. A compound having the structure of Formula III

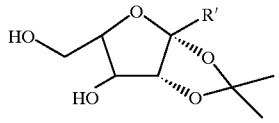

Formula III and its pharmaceutically acceptable salts, esters, enantiomers, diastereomers, N-oxides, amides, or prodrugs, wherein R' is COLDVP, CODVP, COVP or $CH_2$—NH—CO—NHR'', wherein LDVP, DVP and VP represent tripeptide (Leucyl-aspartyl-valyl-prolyl), tripeptide (aspartyl-valyl-prolyl) and (valyl-prolyl), respectively, and wherein R'' is $C_6H_4R'''$-p and R''' is Cl, $NO_2$, $OCH_3$, $CH_3$, $CH_2COOH$, $CH_2COLDVP$, $CH_2CODVP$ or $CH_2COVP$.

4. A compound selected from the group consisting of:

1,2-O-isopropylidene-3-O-dodecyl-5,6-dideoxy-5-N-{[4-(2-hydroxy-2-oxoethyl)phenyl]aminccarbonyl amino}-α,D-5-epiglucofuranose (compound 1), 1,2-O-isopropylidene-3-O-decyl-5,6-dideoxy-5-N-{[4-(2-hydroxy-2-oxoethyl)phenyl]aminocarbonyl-amino}-α,D-5-epiglucofuranose (compound 2), 1,2-O-isopropylidene-3-O-heptyl-5,6-dideoxy-5-N-{[4-(2-hydroxy-2-oxoethyl)phenyl]aminocarbonyl-amino}-α,D-5-epiglucofuranose (compound 3), 1,2-O-isopropylidene-3-O-butyl-5,6-dideoxy-5-N-{[4-(2-hydroxy-2-oxoethyl)phenyl]aminocarbonyl-amino}-α,D-5-epiglucofuranose (compound 4), 1,2-O-isopropylidene-3-O-dodecyl-5,6-dideoxy-5-N-{[4-chlorophenyl]aminocarbonylamino)}α,D-5-epiglucofuranose (compound 5), 1,2-O-isopropylidene-3-O-decyl-5,6-dideoxy-5-N-{[4-chlorophenyl]aminocarbonylamino}α,D-5-epiglucofuranose (compound 6), 1,2-O-isopropylidene-3-O-heptyl-5,6-dideoxy-5-N-{[4-chlorophenyl]aminocarbonylamino}α,D-5-epiglucofuranose (compound 7), 1,2-O-isopropylidene-3-O-butyl-5,6-dideoxy-5-N-{[4-chlorophenyl]aminocarbonylamino}α,D-5-epiglucofuranose (compound 8), 1,2-O-isopropylidene-3-O-dodecyl-5,6-dideoxy-5-N-{[4-methoxyphenyl]aminocarbonylamino}α,D-5-epiglucofuranose (compound 9), 1,2-O-isopropylidene-3-O-decyl-5,6-dideoxy-5-N-{[4-methoxyphenyl]aminocarbonylamino}α,D-5-epiglucofuranose (compound 10), 1,2-O-isopropylidene-3-O-heptyl-5,6-dideoxy-5-N-{[4-methoxyphenyl]aminocarbonylamino}α,D-5-epiglucofuranose (compound 11), 1,2-O-isopropylidene-3-O-butyl-5,6-dideoxy-5-N-{[4-methoxyphenyl]aminocarbonylamino}α,D-5-epiglucofuranose (compound 12), 1,2-O-isopropylidene-3-O-dodecyl-5,6-dideoxy-5-N-{[4-tolyl]aminocarbonylamino}α,D-5-epiglucofuranose (compound 13), 1,2-O-isopropylidene-3-O-decyl-5,6-dideoxy-5-N-{[4-tolyl]aminocarbonylamino}α,D-5-epiglucofuranose (compound 14), 1,2-O-isopropylidene-3-O-heptyl-5,6-dideoxy-5-N-{[4-tolyl]aminocarbonylamino}α,D-5-epiglucofuranose (compound 15), 1,2-O-isopropylidene-3-O-butyl-5,6-dideoxy-5-N-{[4-tolyl]aminocarbonylamino}α,D-5-epiglucofuranose (compound 16), 1,2-O-isopropylidene-3-O-dodecyl-5,6-dideoxy-5-N-{[4-(2-hydroxy-2-oxoethyl)phenyl]aminocarbonylamino}-α,D-5-epiallofuranose (compound 17), 1,2-O-isopropylidene-3-O-decyl-5,6-dideoxy-5-N-{[4-(2-hydroxy-2-oxoethyl)phenylaminocarbonyl-amino}-α,D-5-epiallofuranose (compound 18), 1,2-O-isopropylidene-3-O-heptyl-5,6-dideoxy-5-N-{[4-(2-hydroxy-2-oxoethyl)phenyl]aminocarbonyl-amino}-α,D-5-epiallofuranose (compound 19), 1,2-O-isopropylidene-3-O-butyl-5,6-dideoxy-5-N-{[4-(2-hydroxy-2-oxoethyl)phenyl]aminocarbonylamino}-α,D-5-epiallofuranose (compound 20), 1,2-O-isopropylidene-3-O-dodecyl-5,6-dideoxy-5-N-{[4-chlorophenyl]aminocarbonylamino}α,D-5-epiallofuranose (compound 21), 1,2-O-isopropylidene-3-O-decyl-5,6-dideoxy-5-N-{[4-chlorophenyl]aminocarbonylamino}α,D-5-epiallofuranose (compound 22), 1,2-O-isopropylidene-3-O-heptyl-5,6-dideoxy-5-N-{[4-chlorophenyl]aminocarbonylamino}α,D-5-epiallofuranose (compound 23), 1,2-O-isopropylidene-3-O-butyl-5,6-dideoxy-5-N-{[4-chlorophenyl]aminocarbonylamino}α,D-5-epiallofuranose (compound 24), 1,2-O-isopropylidene-3-O-dodecyl-5,6-dideoxy-5-N-{[4-methoxyphenyl]aminocarbonylamino}α,D-5-epiallofuranose (compound 25), 1,2-O-isopropylidene-3-O-decyl-5,6-dideoxy-5-N-{[4-methoxyphenyl]aminocarbonylamino}α,D-5-epiallofuranose (compound 26), 1,2-O-isopropylidene-3-O-heptyl-5,6-dideoxy-5-N-{[4-methoxyphenyl]aminocarbonylamino}α,D-5-epiallofuranose (compound 27), 1,2-O-isopropylidene-3-O-butyl-5,6-dideoxy-5-N-{[4-methoxyphenyl]aminocarbonyl amino}α,D-5-epiallofuranose (compound 28), 1,2-O-isopropylidene-3-O-dodecyl-5,6-dideoxy-5-N-{[4-tolyl]aminocarbonylamino}α,D-5-epiallofuranose (compound 29),
1,2-O-isopropylidene-3-O-decyl-5,6-dideoxy-5-N-{[4-tolyl]aminocarbonylamino}α,D-5-epiallofuranose (compound 30),
1,2-O-isopropylidene-3-O-heptyl-5,6-dideoxy-5-N-{[4-tolyl]aminocarbonylamino}α,D-5-epiallofuranose (compound 31),
1,2-O-isopropylidene-3-O-butyl-5,6-dideoxy-5-N-{[4-tolyl]aminocarbonylamino}α,D-5-epiallofuranose (compound 32),
2,3-O-isopropylidene-1-O-butyl-5,6-dideoxy-5-N-{[4-(2-hydroxy-2-oxoethyl)phenyl]aminocarbonylamino}-α,D-5-epimannofuranoside (compound 33),
2,3-O-isopropylidene-1-O-hexyl-5,6-dideoxy-5-N-{[4-(2-hydroxy-2-oxoethyl)phenyl]aminocarbonylamino}-α,D-5-epimannofuranoside (compound 34),
2,3-O-isopropylidene-1-O-heptyl-5,6-dideoxy-5-N-{[4-(2-hydroxy-2-oxoethyl)phenyl]aminocarbonylamino}-α,D-5-epimannofuranoside (compound 35),
2,3-O-isopropylidene-1-O-decyl-5,6-dideoxy-5-N-{[4-(2-hydroxy-2-oxoethyl)phenyl]aminocarbonylamino}-α,D-5-epimannofuranoside (compound 36),
2,3-O-isopropylidene-1-O-dodecyl-5,6-dideoxy-5-N-{[4-(2-hydroxy-2-oxoethyl)phenyl]aminocarbonyl-amino}-α,D-5-epimannofuranoside (compound 37),
2,3-O-isopropylidene-1-O-butyl-5,6-dideoxy-5-N-{[4-chlorophenyl]aminocarbonylamino}-α,D-5-epimannofuranoside (compound 38),
2,3-O-isopropylidene-1-O-hexyl-5,6-dideoxy-5-N-{[4-chlorophenyl]aminocarbonylamino}-α,D-5-epimannofuranoside (compound 39),
2,3-O-isopropylidene-1-O-heptyl-5,6-dideoxy-5-N-{[4-chlorophenyl]aminocarbonylamino}-α,D-5-epimannofuranoside (compound 40),
2,3-O-isopropylidene-1-O-decyl-5,6-dideoxy-5-N-{[4-chlorophenyl]aminocarbonylamino}-α,D-5-epimannofuranoside (compound 41),
2,3-O-isopropylidene-1-O-dodecyl-5,6-dideoxy-5-N-{[4-chlorophenyl]aminocarbonylamino}-α,D-5-epimannofuranoside (compound 42),
2,3-O-isopropylidene-1-O-butyl-5,6-dideoxy-5-N-{[4-methoxyphenyl]aminocarbonylamino}-α,D-5-epimannofuranoside (compound 43),
2,3-O-isopropylidene-1-O-hexyl-5,6-dideoxy-5-N-{[4-methoxyphenyl]aminocarbonylamino}α,D-5-epimannofuranoside (compound 44),
2,3-O-isopropylidene-1-O-heptyl-5,6-dideoxy-5-N-{[4-methoxyphenyl]aminocarbonylamino}-α,D-5-epimannofuranoside (compound 45),
2,3-O-isopropylidene-1-O-decyl-5,6-dideoxy-5-N-{[4-methoxyphenyl]aminocarbonylamino}-α,D-5-epimannofuranoside (compound 46),
2,3-O-isopropylidene-1-O-dodecyl-5,6-dideoxy-5-N-{[4-methoxyphenyl]aminocarbonylamino}-α,D-5-epimannofuranoside (compound 47),
2,3-O-isopropylidene-1-O-butyl-5,6-dideoxy-5-N-{[4-tolyl]aminocarbonylamino}-α,D-5-epimannofuranoside (compound 48),
2,3-O-isopropylidene-1-O-hexyl-5,6-dideoxy-5-N-{[4-tolyl]aminocarbonylamino}-α,D-5-epimannofuranoside (compound 49),
2,3-O-isopropylidene-1-O-heptyl-5,6-dideoxy-5-N-{[4-tolyl]aminocarbonylamino}-α,D-5-epimannofuranoside (compound 50),
2,3-O-isopropylidene-1-O-decyl-5,6-dideoxy-5-N-{[4-tolyl]aminocarbonylamino}-α,D-5-epimannofuranoside (compound 51),
2,3-O-isopropylidene-1-O-dodecyl-5,6-dideoxy-5-N-{[4-tolyl]aminocarbonylamino}-α,D-5-epimannofuranoside (compound 52),
1,2-O-isopropylidene-3-O-dodecyl-5-deoxy-5-N-{[4-(2-hydroxy-2-oxoethyl)phenyl]aminocarbonylamino}-α,D-xylofuranose (compound 53),
1,2-O-isopropylidene-3-O-decyl-5-deoxy-5-N-{[4-(2-hydroxy-2-oxoethyl)phenyl]aminocarbonylamino}-α,D-xylofuranose (compound 54),
1,2-O-isopropylidene-3-O-hexyl-5-deoxy-5-N-{[4-(2-hydroxy-2-oxoethyl)phenyl]aminocarbonylamino}-α,D-xylofuranose (compound 55),
1,2-O-isopropylidene-3-O-butyl-5-deoxy-5-N-{[4-(2-hydroxy-2-oxoethyl)phenyl]aminocarbonylamino}-α,D-xylofuranose (compound 56),
1,2-O-isopropylidene-3-O-methyl-5-deoxy-5-N-{[4-(2-hydroxy-2-oxoethyl)phenyl]aminocarbonylamino}-α,D-xylofuranose (compound 57),
1,2-O-isopropylidene-3-O-dodecyl-5-deoxy-5-N-{[4-chlorophenyl]aminocarbonylamino}α,D-xylofuranose (compound 58),
1,2-O-isopropylidene-3-O-decyl-5-deoxy-5-N-{[4-chlorophenyl]aminocarbonylamino}α,D-xylofuranose (compound 59),
1,2-O-isopropylidene-3-O-hexyl-5-deoxy-5-N-{[4-chlorophenyl]aminocarbonylamino}α,D-xylofuranose (compound 60),
1,2-O-isopropylidene-3--butyl-5-deoxy-5-N-{[4-chlorophenyl]aminocarbonylamino}α,D-xylofuranose (compound 61),
1,2-O-isopropylidene-3-O-methyl-5-deoxy-5-N-{[4-chlorophenyl]aminocarbonylamino}α,D-xylofuranose (compound 62),
1,2-O-isopropylidene-3-O-dodecyl-5-deoxy-5-N-{[4-methoxyphenyl]aminocarbonylamino}α,D-xylofuranose (compound 63),
1,2-O-isopropylidene-3-O-decyl-5-deoxy-5-N-{[4-methoxyphenyl]aminocarbonylamino}α,D-xylofuranose (compound 64),
1,2-O-isopropylidene-3-O-hexyl-5-deoxy-5-N-{[4-methoxyphenyl]aminocarbonylamino}α,D-xylofuranose (compound 65),
1,2-O-isopropylidene-3-O-butyl-5-deoxy-5-N-{[4-methoxyphenyl]aminocarbonylamino}α,D-xylofuranose (compound 66),
1,2-O-isopropylidene-3-O-methyl-5-deoxy-5-N-{[4-methoxyphenyl]aminocarbonylamino}α,D-xylofuranose (compound 67),
1,2-O-isopropylidene-3-O-dodecyl-5-deoxy-5-N-{[4-tolyl]aminocarbonylamino}α,D-xylofuranose (compound 68),
1,2-O-isopropylidene-3-O-decyl-5-deoxy-5-N-{[4-tolyl]aminocarbonylamino}α,D-xylofuranose (compound 69),
1,2-O-isopropylidene-3-O-hexyl-5-deoxy-5-N-{[4-tolyl]aminocarbonylamino}α,D-xylofuranose (compound 70),
1,2-O-isopropylidene-3-O-butyl-5-deoxy-5-N-{[4-tolyl]aminocarbonylamino}α,D-xylofuranose (compound 71),
1,2-O-isopropylidene-3-O-methyl-5-deoxy-5-N-{[4-tolyl]aminocarbonylamino}α,D-xylofuranose (compound 72),
1,2-O-isopropylidene-3-O-dodecyl-5 -deoxy-5-N-{[aminocarbonylamino]phenylacetyl-L-Leucyl-α,L-Aspartyl-L-Valyl-L-Proline}-α,D-xylofuranose (compound 73),
1,2-O-isopropylidene-3-O-dodecyl-5-deoxy-5-N-{[aminocarbonylamino]phenylacetyl-α,L-Aspartyl-L-Valyl-L-Proline)-α,D-xylofuranose (compound 74),
1,2-O-isopropylidene-3-O-dodecyl-5-deoxy-5-N-{[aminocarbonylamino]phenylacetyl-L-Valyl-L-Proline}-α,D-xylofuranose (compound 75), 1,2-O-isopropylidene-3-O-dodecyl-5-deoxy-5-N-{[4-(2-hydroxy-2-oxoethyl)phenyl]aminocarbonylamino}-α,D-ribofuranose (compound 76), 1,2-O-isopropylidene-3-O-decyl-5-deoxy-5-N-{[4-(2-hydroxy-2-oxoethyl)phenyl]aminocarbonylamino}-α,D-ribofuranose (compound 77), 1,2-O-isopropylidene-3-O-heptyl-5-deoxy-5-N-{[4-(2-hydroxy-2-oxoethyl)phenyl]aminocarbonylamino}-α,D-ribofuranose (compound 78), 1,2-O-isopropylidene-3-O-butyl-5-deoxy-5-N-{[4-(2-hydroxy-2-oxoethyl)phenyl]aminocarbonylamino}-α,D-ribofuranose (compound 79), 1,2-O-isopropylidene-3-O-methyl-5-deoxy-5-N-{[4-(2-hydroxy-2-oxoethyl)phenyl]aminocarbonylamino}-α,D-ribofuranose (compound 80), 1,2-O-isopropylidene-3-O-dodecyl-5-deoxy-5-N-{[4-chlorophenyl]aminocarbonylamino}α,D-ribofuranose (compound 81), 1,2-O-isopropylidene-3-O-decyl-5-deoxy-5-N-{[4-chlorophenyl]aminocarbonylamino}α,D-ribofuranose (compound 82), 1,2-O-isopropylidene-3-O-heptyl-5-deoxy-5-N-{[4-chlorophenyl]aminocarbonylamino}α,D-ribofuranose (compound 83), 1,2-O-isopropylidene-3-O-butyl-5-deoxy-5-N-{[4-chlorophenyl]aminocarbonylamino}α,D-ribofuranose (compound 84), 1,2-O-isopropylidene-3-O-methyl-5-deoxy-5-N-{[4-chlorophenyl]aminocarbonylamino}α,D-ribofuranose (compound 85), 1,2-O-isopropylidene-3-O-dodecyl-5-deoxy-5-N-}[4-methoxyphenyl]aminocarbonylamino}α,D-ribofuranose (compound 86), 1,2-O-isopropylidene-3-O-decyl-5-deoxy-5-N-{[4methoxyphenyl]aminocarbonylamino}α,D-ribofuranose (compound 87), 1,2-O-isopropylidene-3-O-heptyl-5-deoxy-5-N-{[4-methoxyphenyl]aminocarbonylamino}α,D-ribofuranose (compound 88), 1,2-O-isopropylidene-3-O-butyl-5-deoxy-5-N-{[4-methoxyphenyl]aminocarbonylamino}α,D-ribofuranose (compound 89), 1,2-O-isopropylidene-3-O-methyl-5-deoxy-5-N-{[4-methoxyphenyl]aminocarbonylamino}α,D-ribofuranose (compound 90), 1,2-O-isopropylidene-3-O-dodecyl-5-deoxy-5-N-{[4-tolyl]aminocarbonylamino}α, D-ribofuranose (compound 91), 1,2-O-isopropylidene-3-O-decyl-5-deoxy-5-N-{[4-tolyl]aminocarbonylamino}α, D-ribofuranose (compound 92), 1,2-O-isopropylidene-3-O-heptyl-5-deoxy-5-N-{[4-tolyl]aminocarbonylamino}α, D-ribofuranose (compound 93), 1,2-O-isopropylidene-3-O-butyl-5-deoxy-5-N-{[4-tolyl]aminocarbonylamino}α, Dribofuranose (compound 94), 1,2-O-isopropylidene-3-O-methyl-5-deoxy-5-N-{[4-tolyl]aminocarbonylamino}α, D-ribofuranose (compound 95), 1,2-O-isopropylidene-3-O-dodecyl-5-deoxy-5-N-{[aminocarbonylaminophenyl]acetyl-L-Leucyl-α,L-Aspartyl-L-Valyl-L-Proline}-α,D-ribofuranose (compound 96), 1,2-O-isopropylidene-3-O-dodecyl-5-deoxy-5-N-{[aminocarbonylaminophenyl]acetyl-α,L-Aspartyl-L-Valyl-L-Proline}-α,D-ribofuranose (compound 97), 1,2-O-isopropylidene-3-O-dodecyl-5-deoxy-5-N-{[aminocarbonylaminophenyl]acetyl-L-Valyl-L-Proline}-α,D-ribofuranose (compound 98), 2,3-O-isopropylidene-1-O-methyl-5-deoxy-5-N-{[4-(2-hydroxy-2-oxoethyl)phenyl]aminocarbonylamino}-α,D-lyxofuranoside (compound 99), 2,3-O-isopropylidene-1-O-butyl-5-deoxy-5-N-{[4-(2-hydroxy-2-oxoethyl)phenyl]aminocarbonylamino}-α,D-lyxofuranoside (compound 100), 2,3-O-isopropylidene-1-O-heptyl-5-deoxy-5-N-{[4-(2-hydroxy-2-oxoethyl)phenyl]aminocarbonylamino}α,D-lyxofuranoside (compound 101), 2,3-O-isopropylidene-1-O-decyl-5-deoxy-5-N-{[4-(2-hydroxy-2-oxoethyl)phenyl]aminocarbonylamino}-α,D-lyxofuranose (compound 102), 2,3-O-isopropylidene-1-O-dodecyl-5-deoxy-5-N-{[4-(2-hydroxy-2-oxoethyl)phenyl]aminocarbonylamino}-α,D-lyxofuranoside (compound 103), 2,3-O-isopropylidene-1-O-methyl-5-deoxy-5-N-{[4-chlorophenyl]aminocarbonylamino}α,D-lyxofuranoside (compound 104), 2,3-O-isopropylidene-1-O-butyl-5-deoxy-5-N-{[4-chlorophenyl]aminocarbonylamino}α,D-lyxofuranoside (compound 105), 2,3-O-isopropylidene-1-O-heptyl-5-deoxy-5-N-{[4-chlorophenyl]aminocarbonylamino}α,D-lyxofuranoside (compound 106), 2,3-O-isopropylidene-1-O-decyl-5-deoxy-5-N-{[4-chlorophenyl]aminocarbonylamino}α,D-lyxofuranoside (compound 107), 2,3-O-isopropylidene-1-O-dodecyl-5-deoxy-5-N-{[4-chlorophenyl]aminocarbonylamino}α,D-lyxofuranoside (compound 108), 2,3-O-isopropylidene-1-O-methyl-5-deoxy-5-N-{[4-methoxyphenyl]aminocarbonylamino}α,D-lyxofuranoside (compound 109), 2,3-O-isopropylidene-1-O-butyl-5-deoxy-5-N-{[4-methoxyphenyl]aminocarbonylamino}α,D-lyxofuranoside (compound 110), 2,3-O-isopropylidene-1-O-heptyl-5-deoxy-5-N-{[4-methoxyphenyl]aminocarbonylamino}α,D-lyxofuranoside (compound 111), 2,3-O-isopropylidene-1-O-decyl-5-deoxy-5-N-{[4-methoxyphenyl]aminocarbonylamino}α,D-lyxofuranoside (compound 112), 2,3-O-isopropylidene-1-O-dodecyl-5-deoxy-5-N-{[4-methoxyphenyl]aminocarbonylamino}α,D-lyxofuranoside (compound 113), 2,3-O-isopropylidene-1-O-methyl-5-deoxy-5-N-{[4-tolyl]aminocarbonylamino}α,D-lyxofuranoside (compound 114), 2,3-O-isopropylidene-1-O-butyl-5-deoxy-5-N-{[4-tolyl]aminocarbonylamino}α,D-lyxofuranoside (compound 115), 2,3-O-isopropylidene-1-O-heptyl-5-deoxy-5-N-{[4-tolyl]aminocarbonylamino}α,D-lyxofuranoside (compound 116), 2,3-O-isopropylidene-1-O-decyl-5-deoxy-5-N-{[4-tolyl]aminocarbonylamino}α,D-lyxofuranoside (compound 117), 2,3-O-isopropylidene-1-O-dodecyl-5-deoxy-5-N-{[4-tolyl]aminocarbonylamino}α,D-lyxofuranoside (compound 118), 2,3-O-isopropylidene-1-O-dodecyl-5-deoxy-5-N-{[aminocarbonylamino]phenylacetyl-L-Leucyl-α,L-Aspartyl-L-Valyl-L-Proline}-α,D-lyxofuranoside (compound 119), 2,3-O-isopropylidene-1-O-dodecyl-5-deoxy-5-N-{[aminocarbonylamino]phenylacetyl-α,L-Aspartyl-L-Valyl-L-Proline}-α,D-lyxofuranoside (compound 120), 2,3-O-isopropylidene-1-O-dodecyl-5-deoxy-5-N-{[aminocarbonylamino]phenylacetyl-L-Valyl-L-Proline}-α,D-lyxofuranoside (compound 121), 2,3;4,6-Di-O-isopropylidene-1-carbonyl-L-Leucyl-α,L-Aspartyl-L-Valyl-LProline-α, L-xylo-2-hexulofuranosonic acid (compound 122), 2,3;4,6-Di-O-isopropylidene-1-carbonyl-α,L-Aspartyl-L-Valyl-LProline-α,L-xylo-2-hexulofuranosonic acid (compound 123), 2,3-O-isopropylidene-1-carbonyl-L-Leucyl-α,L-Aspartyl-L-Valyl-LProline-α,L-xylo-2-hexulofuranosonic acid (compound 124), 2,3-O-isopropylidene-1-carbonyl-α,L-Aspartyl-L-Valyl-L-Proline-α,L-xylo-2-hexulofuranosonic acid (compound 125), 2,3-O-isopropylidene-1-carbonyl-L-Valyl-L-Proline-α,L-xylo-2-hexulofuranosonic acid (compound 126), 2,3;4,6-Di-O-isopropylidene-1-deoxy-1-N-{[4-chlorophenyl]aminocarbonylamino}-α,L-xylo-2-hexulofuranose (compound 127), 2,3;4,6-Di-O-isopropylidene-1-deoxy-1-N-{[4-methoxyphenyl]aminocarbonylamino}-α,L-xylo-2-hexulofuranose (compound 128), 2,3;4,6-Di-O-isopropylidene-1-deoxy-1-N-{[4-tolyl]aminocarbonylamino}-α,L-xylo-2-hexulofuranose (compound 129), 2,3-O-isopropylidene-1-deoxy-1-N-{[4-(2-hydroxy-2oxoethyl))phenylaminocarbonylamino}-α,L-xylo-2-hexulofuranose (compound 130), 2,3-O-isopropylidene-1-deoxy-1-N-{[4-chlorophenyl]aminocarbonylamino}-α,L-xylo-2-hexulofuranose (compound 131), 2,3-O-isopropylidene-1-deoxy-1-N-{[4-methoxyphenyl]aminocarbonylamino}-α,L-xylo-2-hexulofuranose (compound 132), 2,3-O-isopropylidene-1-deoxy-1-N-{[4-tolyl]aminocarbonylamino}-α,L-xylo-2-hexulofuranose (compound 133), 2,3-O-isopropylidene-1deoxy-1-N-{[aminocarbonylaminophenylacetyl-L-Leucyl-α,L-Aspartyl-L-Valyl-L-Proline)}-α,L-xylo-2-hexulofuranose (compound 134), 2,3-O-isopropylidene-1-deoxy-1-N-{[aminocarbonylaminophenylacetyl-α,L-Aspartyl-L-Valyl-L-Proline)}-α,L-xylo-2-hexulofuranose (compound 135), and 2,3-O-isopropylidene-1deoxy-1-N-{[aminocarbonylaminophenylacetyl-L-Valyl-L-Proline)}-α,L-xylo-2-hexulofuranose (compound 136).

5. A pharmaceutical composition comprising a therapeutically effective amount of a compound as defined in claim 1, 2, 3 or 4 and a pharmaceutically acceptable carrier.

6. A method of preventing, inhibiting or suppressing cell adhesion in an animal comprising administering to said animal a therapeutically effective amount of a compound having the structure of Formula I:

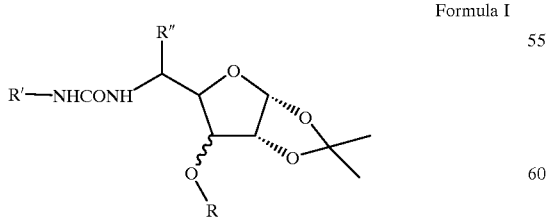

Formula I and its pharmaceutically acceptable salts, esters, enantiomers, diastereomers, N-oxides, amides, or prodrugs, wherein R is $C_1$ to $C_{15}$ alkyl, alkene, straight chain or, aryl, substituted aryl or alkylaryl, R' is $SO_2C_6H_5$, $SO_2C_6H_4CH_3$-p, or $SO_2C_6H_4Cl$-p, phenyl, or $C_6H_4$—R'''-p, wherein R''' is being Cl, $NO_2$, $OCH_3$, $CH_3$, $CH_2COOH$, $CH_2COOCH_3$, $CH_2COLDVP$, $CH_2CODVP$, $CH_2COVP$, wherein LDVP, DVP and VP represent tripeptide (Leucyl-aspartyl-valyl-prolyl), tripeptide (aspartyl-valyl-prolyl) and (valyl-prolyl), respectively, R'' is H or $CH_3$, and (∾∾) represents epiglucofuranose, epiallofuranose, xylofuranose or ribofuranose configurations.

7. A method of preventing, inhibiting or suppressing cell adhesion in an animal comprising administering to said animal a therapeutically effective amount of a compound having the structure of Formula II comprising epimanno-furanoside or lyxofuranoside derivatives

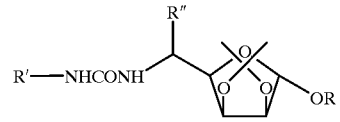

Formula II and its pharmaceutically acceptable salts, esters, enantiomers, diastereomers, N-oxides, amides, or prodrugs, wherein R is $C_1$ to $C_{15}$ alkyl, alkene, straight chain or branched alkyne, aryl, substituted aryl or alkylaryl, R' is $SO_2C_6H_5$, $SO_2C_6H_4CH_3$-p, or $SO_2C_6H_4Cl$-p, phenyl, or $C_6H_4$—R'''-p, wherein R''' is being Cl, $NO_2$, $OCH_3$, $CH_3$, $CH_2COOH$, $CH_2COOCH_3$, $CH_2COLDVP$, $CH_2CODVP$, $CH_2COVP$, wherein LDVP, DVP and VP represent tripeptide (Leucyl-aspartyl-valyl-prolyl), (aspartyl-valyl-prolyl) and (valyl-prolyl), respectively, and R'' is H or $CH_3$.

8. A method of preventing, inhibiting or suppressing cell adhesion in an animal comprising administering to said animal a therapeutically effective amount of a compound having the structure of Formula III:

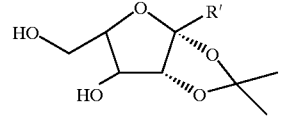

Formula III and its pharmaceutically acceptable salts, esters, enantiomers, diastereomers, N-oxides, amides, or prodrugs, wherein R' is COLDVP, CODVP, COVP or $CH_2$—NH—CO—NHR'', wherein LDVP, DVP and VP represent tripeptide (Leucyl-aspartyl-valyl-prolyl), tripeptide (aspartyl-valyl-prolyl) and (valyl-prolyl), respectively, and wherein R'' is $C_6H_4R'''$-p and R''' is Cl, $NO_2$, $OCH_3$, $CH_3$, $CH_2COOH$, $CH_2COLDVP$, $CH_2CODVP$ or $CH_2COVP$.

9. A method for treating an animal a therapeutically effective amount of suffering from bronchial asthma, rheumatoid arthritis, multiple sclerosis, type I diabetes, psoriasis, allograft rejection, or other inflammatory and/or autoimmune disorders, comprising administering to said animal a compound of the structure of Formula I:

FORMULA I

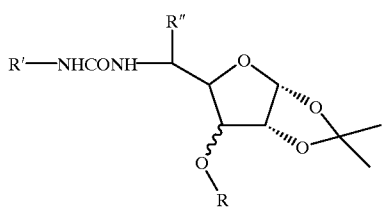

and its pharmaceutically acceptable salts, esters, enantiomers, diastereomers, N-oxides, amides, or prodrugs, wherein R is $C_1$ to $C_{15}$ alkyl, alkene, straight chain alkyne or branched alkyne, aryl, substituted aryl or alkylaryl, R' is $SO_2C_6H_5$, $SO_2C_6H_4CH_3$-p, $SO_2C_6H_4Cl$-p, phenyl, or $C_6H_4$—R'''-p wherein R''' is being Cl, $NO_2$, $OCH_3$, $CH_3$, $CH_2COOH$, $CH_2COOCH_3$, $CH_2COLDVP$, $CH_2CODVP$, $CH_2COVP$, wherein LDVP, DVP and VP represent (Leucyl-aspartyl-valyl-prolyl), (aspartyl-valyl-prolyl) and (valyl-prolyl), respectively, R" is H or $CH_3$, and ( ～～ ) represents idofuranose, talofuranose, xylofuranose or ribofuranose configurations.

10. A method for treating an animal suffering from bronchial asthma, rheumatoid arthritis, multiple sclerosis, type I diabetes, psoriasis, allograft rejection, or other inflammatory and/or autoimmune disorders in an animal comprising administering to said animal a therapeutically effective amount of a compound of the structure of Formula II comprising gulofuranoside or lyxofuranoside derivatives

FORMULA II

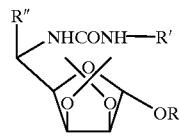

and its pharmaceutically acceptable salts, esters, enantiomers, diastereomers, N-oxides, amides, or prodrugs, wherein R is $C_1$ to $C_{15}$ alkyl, alkene, straight chain alkyne or branched alkyne, aryl, substituted aryl or alkylaryl, R' is $SO_2C_6H_5$, $SO_2C_6H_4CH_3$-p, $SO_2C_6H_4Cl$-p, phenyl, or $C_6H_4$—R'''-p wherein R''' is being Cl, $NO_2$, $OCH_3$, $CH_3$, $CH_2COOH$, $CH_2COOCH_3$, $CH_2COLDVP$, $CH_2CODVP$, $CH_2COVP$, wherein LDVP, DVP and VP represent (Leucyl-aspartyl-valyl-prolyl), (aspartyl-valyl-prolyl) and (valyl-prolyl), respectively, and R" is H or $CH_3$.

11. A method for treating an animal a therapeutically effective amount of suffering from bronchial asthma, rheumatoid arthritis, multiple sclerosis, type I diabetes, psoriasis, allograft rejection, or other inflammatory and/or autoimmune disorders in an animal comprising administering to said animal a compound of the structure of Formula III:

Formula III

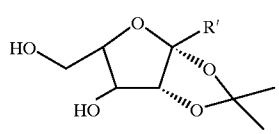

and its pharmaceutically acceptable salts, esters, enantiomers, diastereomers, N-oxides, amides, or prodrugs, wherein R' is COLDVP, CODVP, COVP or $CH_2$—NH—CO—NHR", and R" is $C_6H_4R'''$-p wherein R''' is Cl, $NO_2$, $OCH_3$, $CH_3$, $CH_2COOH$, $CH_2COLDVP$, $CH_2CODVP$ or $CH_2COVP$, wherein LDVP, DVP and VP represent (Leucyl-aspartyl-valyl-prolyl), (aspartyl-valyl-prolyl) and (valyl-prolyl), respectively.

12. A method of preventing, inhibiting or suppressing cell adhesion in an animal comprising the step of administering to said animal a therapeutically effective amount of the pharmaceutical composition according to claim 5.

13. A method of preventing, inhibiting or suppressing cell adhesion-associated inflammation according to claims 9, 10 or 11.

14. A method of preventing, inhibiting or suppressing cell adhesion-associated immune or autoimmune response according to claims 9, 10 or 11.

15. A method of treating or preventing a disease selected from the group consisting of asthma, arthritis, psoriasis, transplantation rejection, multiple sclerosis, diabetes and inflammatory bowel disease according to claims 9, 10 or 11.

16. A process for preparing a compound of Formula I:

Formula I

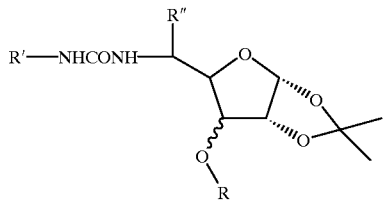

and its pharmaceutically acceptable salts, esters, enantiomers, diastereomers, N-oxides, amides, or prodrugs, wherein R is $C_1$ to $C_{15}$ alkyl, alkene, straight chain alkyne or branched alkyne, aryl, substituted aryl or alkylaryl, R' is $SO_2C_6H_5$, $SO_2C_6H_4CH_3$-p, or $SO_2C_6H_4Cl$-p, phenyl, or $C_6H_4$—R'''-p wherein R''' is being Cl, $NO_2$, $OCH_3$, $CH_3$, $CH_2COOH$, $CH_2COOCH_3$, $CH_2COLDVP$, $CH_2CODVP$, $CH_2COVP$ wherein LDVP, DVP and VP represent tripeptide (Leucyl-aspartyl-valyl-prolyl), tripeptide (aspartyl-valyl-prolyl) and (valyl-prolyl), respectively, R" is $CH_3$, and (～～) represents epiglucofuranose, epiallofuranose, xylofuranose or ribofuranose configurations, which method comprises the steps of:
(A) reacting a compound of Formula IV

FORMULA IV

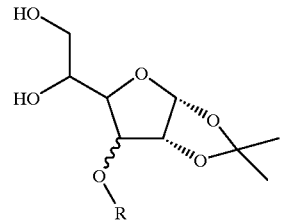

with p-toluene sulphonyl chloride followed by reduction with lithium aluminium hydride (LAH) to obtain the compound of Formula V

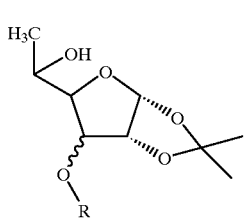

FORMULA V (B) treating the compound of Formula V with p-toluene sulfonyl chloride followed by sodium azide and lithium aluminum hydride to obtain a compound of Formula VI

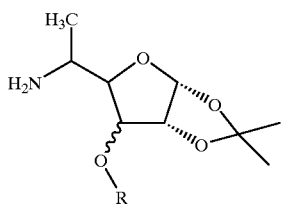

FORMULA VI and (C) reacting the compound of Formula VI with an appropriate isocyanate to obtain the compound of Formula I.

17. A process for preparing a compound of Formula I:

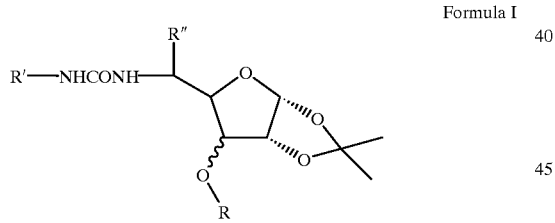

Formula I and its pharmaceutically acceptable salts, esters, enantiomers, diastereomers, N-oxides, amides, prodrugs, wherein R is $C_1$ to $C_{15}$ alkyl, alkene, straight chain alkyne or branched alkyne, aryl, substituted aryl or alkylaryl, R' is $SO_2C_6H_5$, $SO_2C_6H_4CH_3$-p, or $SO_2C_6H_4Cl$-p, phenyl or substituted phenyl, represented as C6H4—R'''-p, R''' being Cl, $NO_2$, $OCH_3$, $CH_3$, $CH_2COOH$, $CH_2COOCH_3$, $CH_2COLDVP$, $CH_2CODVP$, $CH_2COVP$, wherein LDVP, DVP and VP represent tetrapepide (Leucyl-aspartyl-valyl-prolyl), tripeptide (aspartyl-valyl-prolyl) and dipeptide (valyl-prolyl), respectively, R'' is H, and (∼∼∼) represents epiglucofuranose, epiallofuranose, xylofuranose or ribofuranose configurations, which method comprises the steps of:

(A) oxidising 1,2-O-isopropylidene-6-deoxy-3-O-alkyl, alkene, alkyne (straight chain or branched), aryl, substituted aryl or alkyl aryl, α,D-glucofuranose or α,D-allofuranore represented by Formula IV:

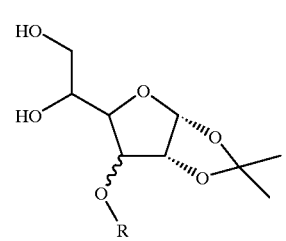

FORMULA IV to obtain the compound of Formula VII:

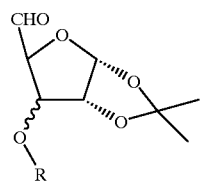

FORMULA VII (B) reducing the compound of Formula VII to obtain the corresponding α,D-ribofuranose or α,D-ribofuranose derivatives of Formula IX:

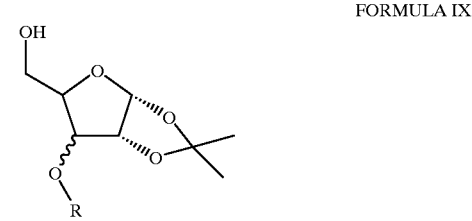

FORMULA IX (C) tosylating the compound of Formula IX with p-toluene sulphonyl chloride;

(D) reacting the product of such reaction with sodium azide;

(E) reducing the product of step D with lithium aluminium hydride to obtain desired amine of Formula X:

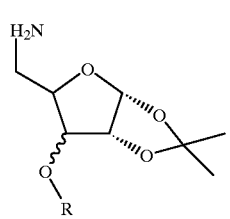

FORMULA X and (F) reacting the amine of Formula X with appropriate isocyanates to obtain the compounds of Formula I.

18. A process for preparing a compound of the Formula I:

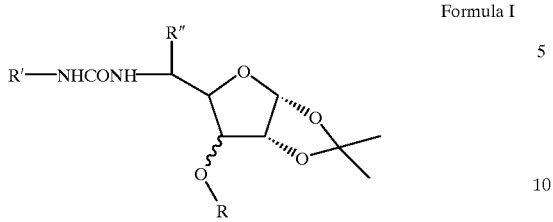

Formula I and its pharmaceutically acceptable salts, esters, enantiomers, diastereomers, N-oxides, amides, or prodrugs, wherein R is $C_1$ to $C_{15}$ alkyl, alkene, straight chain alkyne or branched alkyne, aryl, substituted aryl or alkylaryl, R' is $SO_2C_6H_5$, $SO_2C_6H_4CH_3$-p, or $SO_2C_6H_4Cl$-p, phenyl or substituted phenyl, represented as $C_6H_4$—R'''-p, R''' being Cl, $NO_2$, $OCH_3$, $CH_3$, $CH_2COOH$, $CH_2COOCH_3$, $CH_2COLDVP$, $CH_2CODVP$, $CH_2COVP$, wherein LDVP, DVP and VP represent tripeptide (Leucyl-aspartyl-valyl-prolyl), tripeptide (aspartyl-valyl-prolyl) and dipeptide (valyl-prolyl), respectively, R" is H, and (∿) represents epiglucofuranose, epiallofuranose, xylofuranose or ribofuranose configurations, which method comprises the steps of:

(A) oxidising 1,2-O-isopropylidene-6-deoxy-3-O-alkyl, alkene, alkyne (straight chain or branched), aryl, substituted aryl or alkyl aryl, α,D-glucofuranose or α,D-allofuranore represented by Formula IV:

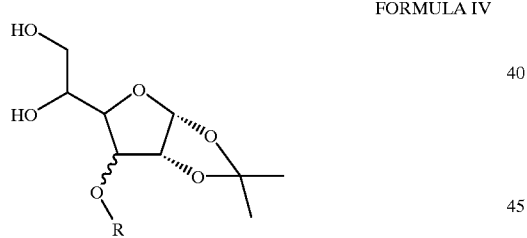

FORMULA IV to obtain the compound of Formula VII:

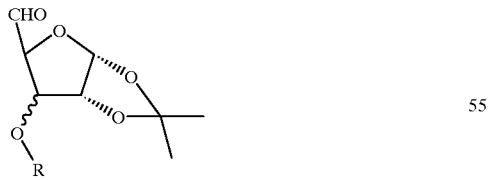

FORMULA VII (B) reacting 1,2-O-isopropylidene-4-carboxaldehydrate-α,D-glucofuranose or allofuranose compound of Formula VII with hydroxylamine hydrochloride;

(C) reducing the product of step B with lithium aluminium hydride to obtain desired amine of Formula X:

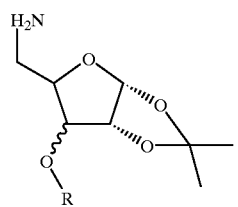

FORMULA X (D) reacting the amine of Formula X with appropriate isocyanates to obtain the compounds of Formula I.

19. A process for preparing compounds of the Formula II comprising epimannofuranoside or lyxofuranoside derivatives

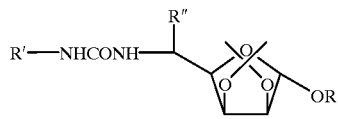

Formula II and its pharmaceutically acceptable salts, esters, enantiomers, diastereomers, N-oxides, amides, or prodrugs, wherein R is $C_1$ to $C_{15}$ alkyl, alkene, straight chain alkyne or branched alkyne, aryl, substituted aryl or alkylaryl, R' is $SO_2C_6H_5$, $SO_2C_6H_4CH_3$-p, or $SO_2C_6H_4Cl$-p, phenyl or substituted phenyl, represented as $C_6H_4$—R'''-p, R''' being Cl, $NO_2$, $OCH_3$, $CH_3$, $CH_2COOH$, $CH_2COOCH_3$, $CH_2COLDVP$, $CH_2CODVP$, $CH_2COVP$, wherein LDVP, DVP and VP represent tetrapepide (Leucyl-aspartyl-valyl-prolyl), tripeptide (aspartyl-valyl-prolyl) and dipeptide (valyl-prolyl), respectively, R" is $CH_3$, which process comprises the steps of:

(A) reacting 2,3-O-isopropylidene-6-deoxy-1-O-alkyl, alkene, alkyne, (straight chain or branched) aryl, substituted aryl or alkylaryl mannofuranoside of Formula XI:

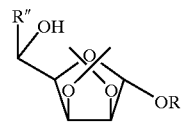

FORMULA XI with p-toluene sulphonylchloride;
(B) reacting the product of step A with sodium azide;
(C) reducing the product of step B with lithium aluminium hydride to obtain the corresponding 5-Deoxy-5-amino epimannofuronoside of Formula XII:

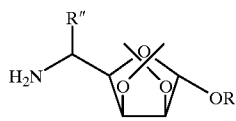

FORMULA XII and (D) treating the compound of Formula XII with appropriate alkyl or aryl or substituted aryl isocyanates to obtain compounds of Formula II.

20. A process of preparing the compounds of Formula II comprising epimannofuranoside or lyxofuranoside derivatives

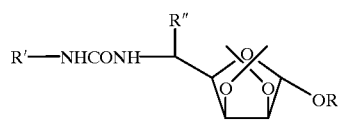
Formula II and its pharmaceutically acceptable salts, esters, enantiomers, diastereomers, N-oxides, amides, or prodrugs, wherein R is $C_1$ to $C_{15}$ alkyl, alkene, straight chain alkyne or branched alkyne, aryl, substituted aryl or alkylaryl, R' is $SO_2C_6H_5$, $SO_2C_6H_4CH_3$-p, or $SO_2C_6H_4Cl$-p, phenyl or substituted phenyl, represented as $C_6H4$—R'''-p, R''' being Cl, $NO_2$, $OCH_3$, $CH_3$, $CH_2COOH$, $CH_2COOCH_3$, $CH_2COLDVP$, $CH_2CODVP$, $CH_2COVP$, wherein LDVP, DVP and VP represent tetrapepide (Leucyl-aspartyl-valyl-prolyl), tripeptide (aspartyl-valyl-prolyl) and depeptide (valyl-prolyl), respectively, R'' is H, which process comprises the steps of (A) treating 2,3-O-isopropylidene-5-deoxy-1-O-alkyl, alkene, alkyne (straight chain or branched), aryl, substituted aryl or alkylaryl)-5-tosyl-α-D-lyxofuranoside of Formula XIII:

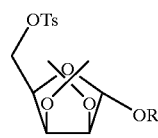
FORMULA XIII with sodium azide;

(B) reducing the compound of Formula XIII with lithium aluminium hydride to obtain the desired amine of Formula XIV

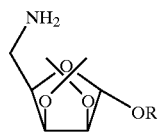
FORMULA XIV and (C) treating the compound of Formula XIV with an appropriate isocyanate to obtain the compounds of Formula II.

21. A process for preparing the compounds of Formula III

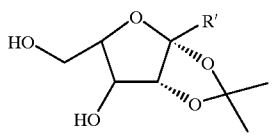
FORMULA III and its pharmaceutically acceptable salts, esters, enantiomers, diastereomers, N-oxides, amides, prodrugs, wherein R' is $CH_2$—NH—CO—NHR'', and wherein R'' is $C_6H_4R'''$-p wherein R''' is Cl, $NO_2$, $OCH_3$, $CH_3$, $CH_2COOH$,

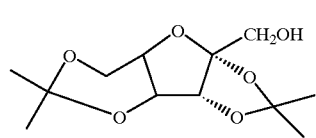
FORMULA XVI $CH_2COLDVP$, $CH_2CODVP$ or $CH_2COVP$, which process comprises the steps of:

(A) treating 2,3;4,6-Di-O-isopropylidene-α,L-xylo-2-hexulofuranose of Formula XVI:
with p-toluene sulphonyl chloride to obtain the compound of Formula XVII:

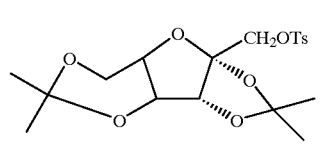
FORMULA XVII (B) reacting the compound of Formula XVII with sodium azide and lithium aluminium hydride to obtain the corresponding 1-amino derivatives of Formula XIX:

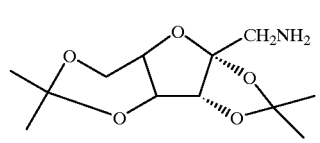
FORMULA XIX (C) treating the compound of Formula XIX with an appropriate isocyanate; and (D) hydrolysing selectively the 4,6-positions of the product of step C to obtain the compounds of Formula III.

22. A process to prepare compounds of Formula III

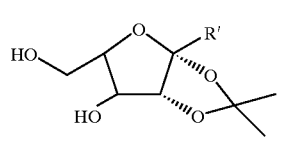
Formula III and its pharmaceutically acceptable salts, esters, enantiomers, diastereomers, N-oxides, amides, or prodrugs, wherein R' is COLDVP or CODVP wherein LDVP, DVP and VP represent tetrapepide (Leucyl-aspartyl-valyl-prolyl), tripeptide (aspartyl-valyl-prolyl) and dipeptide (valyl-prolyl), respectively, and wherein R'' is $C_6H_4R'''$-p wherein R''' is Cl, $NO_2$, $OCH_3$, $CH_3$, $CH_2COOH$, $CH_2COLDVP$, $CH_2CODVP$ or $CH_2COVP$, which process comprises the steps of (A) reacting 2,3;4,6-Di-O-isopropylidene-α,L-xylo-2-hexulofuranosonic acid of Formula XV:

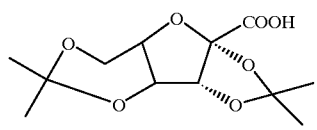
FORMULA XV
with LD (OBzl) VP (OBzl);
(B) hydrogenating the compound of Formula XV to obtain the compounds of Formula XXI:
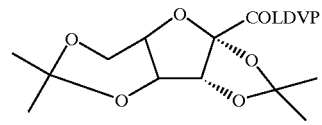
FORMULA XXI
(C) hydrolysing selectively the compound of Formula XXI with perchloric acid to obtain the compounds of Formula III.
* * * * *